United States Patent
Heaton et al.

(10) Patent No.: US 8,392,419 B2
(45) Date of Patent: Mar. 5, 2013

(54) COMPUTER RESEARCH TOOL FOR THE ORGANIZATION, VISUALIZATION AND ANALYSIS OF METABOLIC-RELATED CLINICAL DATA AND METHOD THEREOF

(75) Inventors: Kelly Heaton, Millwood, VA (US); Amy Killoren Clark, Lully (CH); Luc Girardin, Zurich (CH); Dominik Brodbeck, Rifferswill (CH)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 12/949,201

(22) Filed: Nov. 18, 2010

(65) Prior Publication Data

US 2011/0191343 A1 Aug. 4, 2011

Related U.S. Application Data

(63) Continuation of application No. PCT/EP2009/044293, filed on May 18, 2009.

(51) Int. Cl.
*G06F 17/30* (2006.01)
(52) U.S. Cl. .................. 707/737; 370/342; 375/152
(58) Field of Classification Search .......... 707/737; 370/342
See application file for complete search history.

(56) References Cited

U.S. PATENT DOCUMENTS

| 6,611,846 | B1 | 8/2003 | Stoodley |
| 2007/0073559 | A1* | 3/2007 | Stangel ............... 705/2 |
| 2007/0118399 | A1* | 5/2007 | Avinash et al. .......... 705/2 |
| 2008/0091471 | A1* | 4/2008 | Michon et al. ........... 705/3 |

FOREIGN PATENT DOCUMENTS

| WO | 2004008273 A2 | 1/2004 |
| WO | 2005038691 A2 | 4/2005 |

OTHER PUBLICATIONS

McDonnell, et al., "A Novel Approach to Continuous Glucose Analysis Utilizing Glycemic Variation", Diabetes Technology & Therapeutics, vol. 7, No. 2, 2005, pp. 253-263.
Kovatchev, et al., "Quantifying Temporal Glucose Variability in Diabetes via Continuous Glucose Monitoring: Mathematical Methods and Clinical Application", Diabetes Technology & Therapeutics, vol. 7, No. 6, 2005, pp. 849-862.
Service, et al., "Measurements of Glucose Control", Diabetes Care, vol. 10, No. 2, Mar.-Apr. 1987, pp. 225-237.

* cited by examiner

*Primary Examiner* — Shyue Jiunn Hwa
(74) *Attorney, Agent, or Firm* — Dinsmore & Shohl LLP

(57) ABSTRACT

A computer research tool for inputting, searching, displaying, and analyzing metabolic-related clinical data utilizing a novel graphical user interface (GUI) for visual-statistical data analysis and insight generation and method thereof are disclosed.

18 Claims, 15 Drawing Sheets

| TITLE | Info | TAGS | TIME-SER... | EPOCH | ELEMENT | ARM | | HbA1c (%) | BODY MASS INDEX | SEX | AGE |
|---|---|---|---|---|---|---|---|---|---|---|---|
| GROUPS | | | | | | | | | | | |
| T2 DIABETIC | | | | | | | | | | | |
| DIET STUDY | | | | | | | | | | | |
| BASELINE | | | | | | | | | | | |
| DENISE [1] - COPY | | | CGM | BASELINE | B SLOW FIRST | 1 B SLOW FIRST GROUP | 1 | ◄ 5.7 | 29.1 | F | 50 |
| DANNY [1] - COPY | | | CGM | BASELINE | B SLOW FIRST | 1 B SLOW FIRST GROUP | 1 | ◄ 6.1 | 35.1 | M | 50 |
| DORIS [1] - COPY | | | CGM | BASELINE | A FAST FIRST | 1 A FAST FIRST GROUP | 1 | ◄ 6.1 | 27.1 | F | 60 |
| DANIEL [1] - COPY | | | CGM | BASELINE | A FAST FIRST | 1 A FAST FIRST GROUP | 1 | ◄ 6.2 | 32.2 | M | 59 |
| DEBORAH [1] - COPY | | MAX GLUCOSE >1... | CGM | BASELINE | B SLOW FIRST | 1 B SLOW FIRST GROUP | 1 | ◄ 6.2 | 38.2 | F | 58 |
| DONALD [1] - COPY | | | CGM | BASELINE | A FAST FIRST | 1 A FAST FIRST GROUP | 1 | ◄ 6.3 | 28.4 | M | 67 |
| DALE [1] - COPY | | | CGM | BASELINE | A FAST FIRST | 1 A FAST FIRST GROUP | 1 | ◄ 6.4 | 27.3 | M | 62 |
| DOUGLAS [1] - COPY | | | CGM | BASELINE | A FAST FIRST | 1 A FAST FIRST GROUP | 1 | ◄ 6.4 | 32.0 | M | 72 |
| DARRELL [1] - COPY | | | CGM | BASELINE | A FAST FIRST | 1 A FAST FIRST GROUP | 1 | ◄ 6.6 | 28.5 | M | 65 |
| DOLORES [1] - COPY | | MAX GLUCOSE >1... | CGM | BASELINE | A FAST FIRST | 1 A FAST FIRST GROUP | 1 | ◄ 6.7 | 26.3 | F | 67 |
| DYLAN [1] - COPY | | MAX GLUCOSE >1... | CGM | BASELINE | A FAST FIRST | 1 A FAST FIRST GROUP | 1 | ◄ 6.8 | 26.9 | M | 68 |
| DEREK [1] - COPY | | | CGM | BASELINE | B SLOW FIRST | 1 B SLOW FIRST GROUP | 1 | ◄ 7.9 | 31.5 | M | 50 |
| DWIGHT [1] - COPY | | MAX GLUCOSE >1... | CGM | BASELINE | B SLOW FIRST | 1 B SLOW FIRST GROUP | 1 | ◄ 7.9 | 30.4 | M | 66 |
| DIRK [1] - COPY | | | CGM | BASELINE | A FAST FIRST | 1 A FAST FIRST GROUP | II | ◄ 8.7 | 23.6 | M | 60 |
| DEAN [1] - COPY | | | CGM | BASELINE | B SLOW FIRST | 1 B SLOW FIRST GROUP | II | ◄ 9.5 | 38.9 | M | 66 |
| DAVID [1] - COPY | | | CGM | BASELINE | B SLOW FIRST | 1 B SLOW FIRST GROUP | II | ◄ 9.9 | 28.5 | M | 46 |

COMPUTER RESEARCH TOOL FOR THE ORGANIZATION, VISUALIZATION AND ANALYSIS OF METABOLIC-RELATED CLINICAL DATA AND METHOD THEREOF

CROSS-REFERENCE TO RELATED APPLICATIONS

This application is a continuation of International Application No. PCT/EP2009/044293 filed on May 18, 2009 which claims priority to U.S. Provisional Application No. 61/054,184 filed on May 19, 2008.

TECHNICAL FIELD

The embodiments of the present disclosure relate to computer-aided medical research, and more specifically to a computer research tool for the organization, visualization and analysis of metabolic-related clinical data and a method thereof.

Diagnostic data such as, for example, metabolic-related clinical data, contains a wealth of information about human beings, ranging from physiological to behavioral to circumstantial. Interpreting diagnostic information therefore involves two categories of insight: (1) Contextual—from whom did the data come, how was it technically recorded, and under what circumstances was it collected; and (2) Relational—how does the data compare with established norms and other data of comparable characteristics.

Numerous clinical studies using consumer continuous glucose monitoring (CGM) have yielded knowledge about monitoring technologies as well as the physiology of people with diabetes. Nevertheless, there is little or no coordinated effort to explore this clinical data for cross-study comparisons or insight generation. Such data is simply not categorized or organized in a format that is useable or shareable among the CGM community.

Conventional methods of categorizing data, generally speaking, follow two approaches: lumping and splitting. Both approaches are useful, but each places a different conceptual constraint on the understanding and navigability of data. "Lumping" establishes broad categories and general trends, but a user, such as a researcher, may overlook subtle, individual differences in the data. "Splitting" establishes precise definitions and specific categories, but a user may lose the big picture and create unwieldy complexity. For example, a data "lumper" would argue that breakfast, lunch and dinner are all "meals" and should therefore be treated equally; a "splitter" would argue that each type of meal is unique and requires a separate category of definition. The risk of lumping data is that important differences are lost to averaging. The risk of splitting data is that too much complexity impedes its usefulness in decision-making or pattern recognition.

Likewise, highly structured and highly flexible methods of organizing data offer distinct advantages and disadvantages to the user. A hierarchical system for data organization, such as a Microsoft's Windows Explorer, enables the user to create structured storage for their electronic files in the form of hierarchical folders. The advantage of such as system is the logical ordering of data introduced by appropriately labeled and nested file folders. The disadvantage is that files can become easily lost within the folder hierarchy unless the user remembers the precise file name or location. Over time and with large amounts of data, certain information gets lost or forgotten in the filing structure.

A highly flexible filing system, such as computerized systems for tagging or assigning metadata to a file, enables the user to associate descriptive keywords with files in a non-hierarchical structure of data management. Files carrying the same tags can be clustered together in "tag clouds" to show relationships, including files that share multiple tags in common (or not). However, one problem with such tagging systems is that typically, there is no information about the meaning of the tags (no common definition among different users) and this can lead to misunderstanding, mislabeling, and multiple synonymous tags to represent the same concept, and/or inappropriate connections between files. For example, an episode of physical activity may be equally tagged "sports," "jogging," "running," or "workout," all of which are concepts intended to represent the same event. Variable names for the same Tag concept can also cause lost data in the system, such as "hypoglycemia" or "hypo," which is likely intended to represent the same concept, but do not aggregate in tag clouds because their spelling is different. In addition, the flexibility of tagging enables people to label their data in a way that they personally find meaningful, but usually, multiple keywords are required to catch all of the relevant data, the variation in individual terminology can make it difficult to obtain a comprehensive view of data that is thematically related, and the probability for data loss is high.

SUMMARY

The problems and needs mentioned in the above background are addressed by the embodiments of the present disclosure providing a computer research tool for the organization, visualization and analysis of metabolic-related clinical data and a method thereof. One feature of the embodiments of the present disclosure is the combined use of Groups and Tags. As disclosed herein, Groups impose a hierarchical structure on the metabolic-related clinical data whereas Tags impose flexible descriptions on the data. A user is thereby able to organize such data within a hierarchy of appropriately named Groups and search for all elements that carry the same descriptive Tag within this structured filing system. In this manner, embodiments of the present disclosure offers a unique interface for defining, labeling, organizing and searching discrete time periods with associated data ("Data Memos"). As explained herein, Data Memos can be descriptively named, tagged, copied and grouped into user-defined categories for the purpose of understanding their significance. Embodiments of the present disclosure also provides unique tools for searching and visualizing such tagged and grouped data, i.e., Boolean queries, hierarchical views and interactive graphs.

In addition to the above noted features, embodiments of the present disclosure enhance the effectiveness of statistical analytic methods by facilitating the combination of statistical analytic methods with human visual recognition abilities to identify patterns, trends and relationships, and recognizing that visualizations play an important part in refining and understanding numerical solutions. Embodiments of the present disclosure are also useful for hypothesis generation and knowledge discovery, by facilitating the identification of novel, potentially useful, and ultimately understandable patterns in diagnostic data, such as metabolic-related clinical data, that may contribute to therapeutic applications for general disease management, and in one particular embodiment, to therapeutic applications of continuous glucose monitoring (CGM) for diabetes management. Embodiments of the present disclosure help, insofar as possible, facilitate greater understanding and treatment of metabolic diseases by helping researchers to identify patterns and discover medical insights within a complex database of patient information. For example, a typical complex database of patient information may comprise over a hundred thousand time series data points and related explanatory information (i.e., patient data objects), for instance, generated from collecting physiological measurements from over thirty patients at 1 minute intervals over a multi-day period (e.g., 3-7 days), which typically results in such databases containing over 2 MB of such patient information (which if displayed at the same time would easily overwhelmed a user with too much data).

In one embodiment, the present disclosure provides software i.e. a computer program which has computer-readable program code for instructing a processor of a computer system to implement a computer research tool for the loading, organization, visualization and analysis of metabolic-related clinical data. The computer program according to the present disclosure enables easy exploration of such complex diagnostic data, especially time series glucose data, thereby new data connections and relationships may be discovered. As a result, the user is able to more efficiently and effectively review larger quantities of related clinical information than conventionally possible. The computer program according to the present disclosure also offers tools to select, organize, annotate, visualize and interpret the significance of diagnostic information (e.g., visually by "seeing" a pattern by eye, algorithmically by defining and executing a Boolean search query, or statistically by computing metrics that reveal a pattern mathematically). The computer program according to the present disclosure permits a user to test inventive methods of data visualization and analysis to evaluate their usefulness in consumer healthcare products. The computer program according to the present disclosure enables the sharing of such clinical data with a broader, non-technical audience to promote understanding and communication by use of a graphical user interface (GUI) according to an embodiment of the present disclosure that makes complex data management and analysis accessible to users that do not have a mathematical or computer science background, such as the majority of healthcare practitioners.

Some of the features of the computer program according to the present disclosure provide robust, flexible data visualization options that tailor the communication of complex information for different purposes and audiences (researchers, specialists, DNEs, patients of all ages). Example of such features, as disclosed herein include, Shape Memo, Target Range Analysis, Polar Coordinate Diagrams, Phase Space Diagrams, River Diagrams, and charts. The computer program according to the present disclosure also provides highly intuitive graphical interfaces with simple, clear controls and direct visual feedback that allow manipulation of key parameters for statistical analysis. Examples include the hierarchical view option in Select Table, interactive/clickable graphs available in an Analyze workspace, summary charts for tags and custom event markers to aid in pattern detection, Target Range Analysis, Merged Curves, and Alignment features.

Other features of the computer program according to the present disclosure include automated aids for complex data-intensive operations, such as parsing data or calculating metrics across patient populations and clinical studies, such as for example, macros, automated Data Memo creation and alignment, as well as complex, data-intensive operations such as Boolean searches, Tags summaries and statistics, automatic assignment of a Tag to a Data Memo that is annotated with a Custom Event marker, and also ability to locate all Data Memos that carry a certain Tag and/or Custom Event marker. The computer program according to the present disclosure also provides document reporting tools to export information in a printed format that supports the need for clear communication as well as to export data, including original data and user-added meta-data (e.g., file names, tags, groups, hierarchical organization of groups, color assignments, custom event markers and notes) for further analysis with third party software. Pathway reporting tools to document and validate analysis pathways (i.e., the steps by which a graph, calculation or comparison was made) is also provided as well as guided (wizard) data importing and mapping that supports the user through each step required to load new clinical data into the system implementing the computer program according to the present disclosure and maximize compatibility with the functions of the computer program.

For example, in one embodiment, an apparatus for viewing and organizing patient data objects of a data structure can be provided that comprises a display, a user interface, a memory containing a plurality of patient identifications having associated therewith the patient data objects, which includes patient data, a processor operably connected to the display, the user interface, and the memory, and a program. The program causes the processor to display from memory the plurality of patient identifications and their associated patient data objects on the display for selection via the user interface, to assign in memory the associated patient data object of selected patient identifications to a designated group in a group hierarchy of other designated groups to establish meaningful patterns which characterizes the selected patient data objects to user-specified events defined and undefined originally in the data structure, and to retrieve from memory and display on the display all patient data objects in the group hierarchy. In another embodiment to the above mentioned apparatus, the program further causes the processor to display from memory the patient data objects assigned to the designated group on the display for selection via the user interface, to assign in memory selected patient data objects to a user-defined tag which characterizes the selected patient data objects to a user-specified event undefined originally in the data structure, to receive a specified user-defined tag via the user interface, and to retrieve from memory and display on the display all patient data objects in the group hierarchy that are assigned the specified user-defined tag.

In another embodiment, an apparatus for viewing and organizing patient data objects of a clinical data structure is disclosed. The apparatus comprises a display; a user interface; a memory containing a plurality of patient identifications having associated therewith the patient data objects, the patient data objects including patient physiological data; and a processor operably connected to the display, the user interface, and the memory. The apparatus also includes a program for causing the processor to display from memory the plurality of patient identifications and their associated patient data objects on the display for selection via the user interface, to assign in memory the associated patient data object of selected patient identifications to a designated group in a group hierarchy of other designated groups, to display from memory the patient data objects assigned to the designated group on the display for selection via the user interface, to assign in memory selected patient data objects to a user-defined tag which characterizes the selected patient data objects to a user-specified event undefined originally in the clinical data structure, to receive a specified user-defined tag via the user interface, and to retrieve from memory and display on the display all patient data objects in the group hierarchy that are assigned the specified user-defined tag.

In one embodiment, the program further causes the processor to create in memory a data segment from a time series provided in the patient data objects. In another embodiment, the program further causes the processor to list the group hierarchy on the display for permitting a choosing of one or more designated groups via the user interface and to display all user-defined tags assigned to the patient data objects assigned to the chosen one or more designed groups on the display. In another embodiment, the program further causes the processor to permit both a selection via the user interface of one or more displayed user-defined tags contained in the chosen one or more designed groups and of a query choice which instructs the processor to display on the display as a group the patient data objects belonging to either a union of the one or more chosen designed groups and the selected one or more user-defined tags, or an intersection between the one or more chosen designed groups and the one or more selected user-defined tags. In still another embodiment, the program further causes the processor to display a number adjacent the specified user-defined tag which reflects a cumulative count of all patient data objects carrying the specified designed tag throughout the group hierarchy. In yet another embodiment, the program further causes the processor to permit contextual notes entered via the user interface to be associated in memory with patient data objects. In still another embodiment, the program further causes the processor to display a listing of all user-defined tags in the group hierarchy for selection of one or more user-defined tags via the user interface and to display all data objects assigned the selected user-defined tags.

In another embodiment, deleting a tag removes the tag and all its associations to all assigned patient data objects, wherein the deleting does not delete the patient data objects from their respective designated groups. In still another embodiment, a designated group is a sub-group of one or more of the designated groups. In yet another embodiment, the apparatus further comprises a data source for providing to the memory selected ones of the plurality of patient identifications and the associated patient data objects when requested by the processor. In another embodiment, the apparatus further comprising a data source storing the plurality of patient identifications and associated patient data objects grouped according to a clinical study, wherein the memory receives selected ones of the plurality of patient identifications and the associated patient data objects from the data source according to which one of the at least one clinical study is requested by the processor to be received from the data source. In still another embodiment, the program further causes the processor to display the group hierarchy on the display. In one embodiment, the program further causes the processor to display on the display one of a plurality of workspaces selected via the user interface, said workspaces include a data selection workspace which presents the patient data objects in a table, a visualize workspace which presents glucose traces derived from the patient physiological data provided in the patient data objects, and an analyze workspace which presents a graph of the patient data objects plotted according to variables which further characterize the patient data objects.

In another embodiment, the patient data objects used by the processor in a selected workspace are selected via the user interface from at least one of the designated group, the designated groups, and the specified user-defined tag. In still another embodiment, the program further causes the processor to present on the display a variable selection panel for selecting the variables. In another embodiment, the program further causes the processor to present on the display a time series panel which displays an overlay of the glucose traces. In yet another embodiment, the program further causes the processor to highlight one or more of the patient data objects presented in a selected workspace on the display when chosen via the user interface and to maintain the highlighting of the one or more patient data objects when presenting another one of the workspaces when selected via the user interface. In still another embodiment, patient identifications and patient data objects are selectable via the user interface and assignable in memory to a new designated group and to a new user-defined tag from any one of the workspaces.

In another embodiment, a method of organizing patient data objects using a data processing system having a display, a user interface, a memory, and a processor operably connected to the display, the user interface, and the memory is disclosed. The method comprises receiving into the memory a plurality of patient data objects organized via a clinical data structure from a data source; and operating the processor to: display from memory the plurality of patient identifications and their associated patient data objects on the display for selection via the user interface, assign in memory the associated patient data object of selected patient identifications to a designated group in a group hierarchy of other designated groups, display from memory the patient data objects assigned to the designated group on the display for selection via the user interface, assign in memory selected patient data objects to a user-defined tag which characterizes the selected patient data objects to a user-specified event undefined originally in the clinical data structure, receive a specified user-defined tag via the user interface, and retrieve from memory and display on the display all patient data objects in the group hierarchy that are assigned the specified user-defined tag.

In still another embodiment, a computer readable media containing a program for displaying and organizing patient data objects on a display device of a computer system is disclosed. The patient data objects being obtained from a data source associated with the computer system. The program operates a processor of the computer system to receive into memory the plurality of patient data objects organized via a clinical data structure from a data source, display from memory the plurality of patient identifications and their associated patient data objects on the display for selection via the user interface, assign in memory the associated patient data object of selected patient identifications to a designated group in a group hierarchy of other designated groups, display from memory the patient data objects assigned to the designated group on the display for selection via the user interface, assign in memory selected patient data objects to a user-defined tag which characterizes the selected patient data objects to a user-specified event undefined originally in the clinical data structure, receive a specified user-defined tag via the user interface, and retrieve from memory and display on the display all patient data objects in the group hierarchy that are assigned the specified user-defined tag.

It is to be appreciated that the embodiments of the present disclosure are useful for medical professionals who would like to (1) diagnose a medical condition by comparing one or more patient's data against other patients' data; (2) define new categories of human health and/or disease based on the ordering, visualization and analysis of clinical data; (3) to organize, classify, visualize and analyze a large quantity of patient data for the purposes of ongoing medical research, the practice of evidenced-based medicine and/or the advancement of scientific knowledge; and (4) support or practice Personalized Medicine by tailoring therapy to an individual patient's needs. The embodiments of the disclosure are particularly useful for persons working in the medical field who rely on diagnostic information to characterize their patients' health condition. The usefulness of the embodiments of the disclosure are greatest when combined with large quantities of metabolic diagnostic data, especially demographics, vital signs, laboratory measurements and rich time-series diagnostic data, such as continuously monitored glucose.

These and other features and advantages of the embodiments of the present disclosure will further become apparent from the drawings and detailed description provided hereafter.

BRIEF DESCRIPTION OF THE DRAWINGS

FIGS. 7A and 7B each depicts a select workspace of the graphical user interface of FIG. 5 according to an embodiment of the present disclosure and shown populated with metabolic data, wherein FIG. 7A is displaying objects from the data in a flat table view and FIG. 7B is displaying the objects in a hierarchical view.

FIG. 16 depicts a data findability example according to the present disclosure.

DETAILED DESCRIPTION

Figure 1:
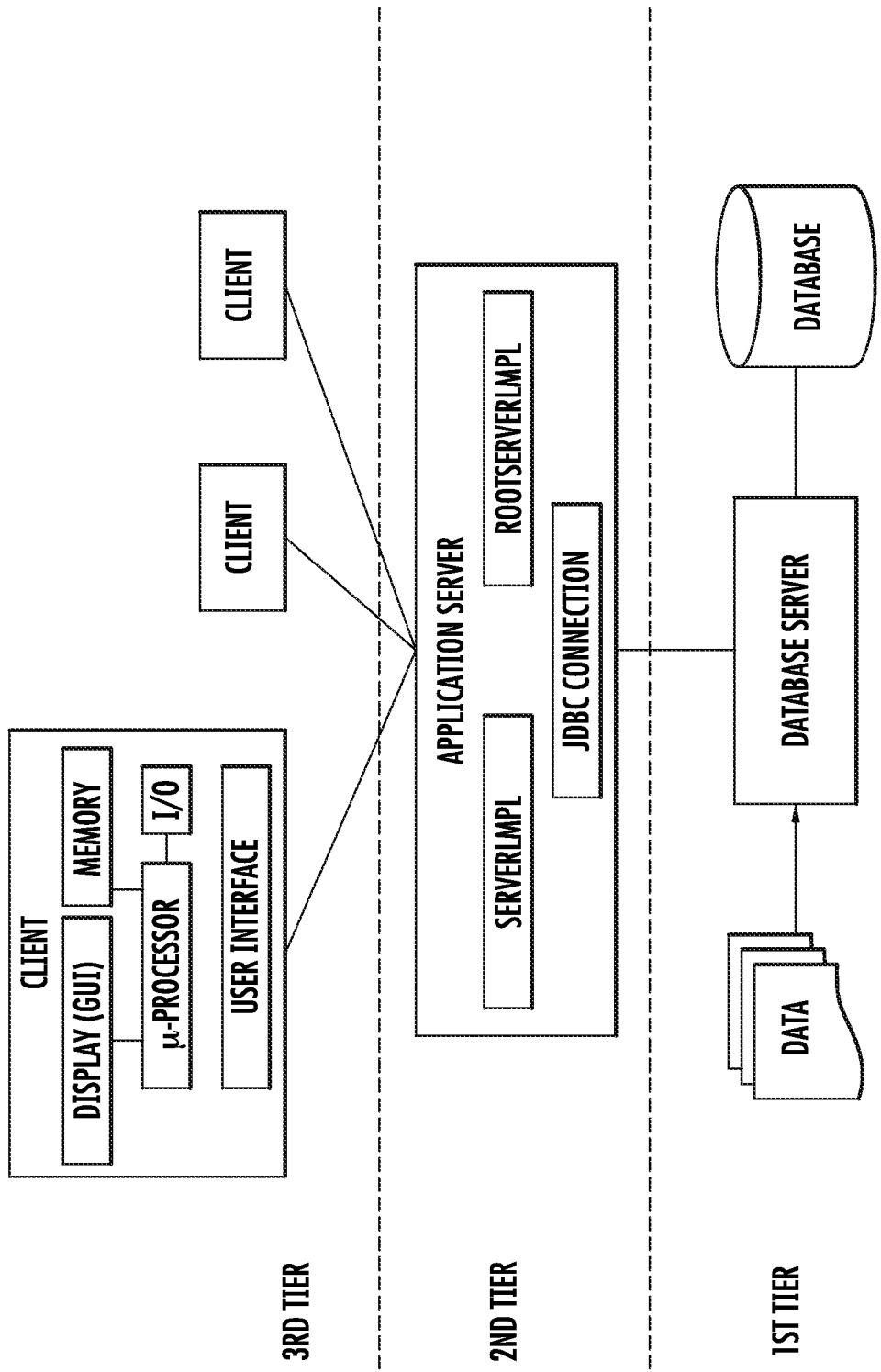
FIG. 1 is a block diagram depicting a classic three tier client/server computer system model utilized in an embodiment of the present disclosure (1-tier/Database Server, 2-tier/Application Server, 3-tier/Client Computer).

As will be appreciated by one of skill in the art, the embodiments of the present disclosure may be embodied as a method, a data processing system, or a computer program product. Accordingly, the embodiments of the present disclosure may take the form of an entirely hardware embodiment, an entirely software embodiment or an embodiment combining software and hardware aspects. Furthermore, some embodiments of the present disclosure may take the form of a computer program product on a computer-readable storage medium having computer-readable program code embodied in the medium. Any suitable computer medium may be utilized including hard disks, CD-ROMs, optical storage devices, magnetic storage devices, or programmable ROM devices.

The present disclosure is described below with reference to illustrations in the figures of methods, apparatus (systems) and computer program products according to embodiments of the invention. It will be understood that each feature or combinations of features in the illustrations of the figures, can be implemented by computer-readable program code. The computer-readable program code may be loaded onto a general purpose computer, special purpose computer, or other programmable data processing apparatus to produce a machine, such that the instructions contain in the code which execute on the computer or other programmable data processing apparatus create means for implementing the functions disclosed herein.

The computer-readable program code for implementing the present invention may be written in various object-oriented programming languages, such as Delphi and Java®. However, it is understood that other object oriented programming languages, such as C++ and Smalltalk, as well as conventional programming languages, such as FORTRAN or COBOL, could be utilized.

Referring now to the drawings, and firstly to FIG. 1, various embodiments of the present disclosure will be described in greater details.

I. Architecture

FIG. 1 is an overview of one embodiment of the hardware architecture for inputting, searching, displaying, and analyzing metabolic-related clinical data utilizing a novel graphical user interface (GUI) for visual-statistical data analysis and insight generation. In this embodiment, the architecture comprises at least two networked computer microprocessors (client component and server component(s)) and a database(s) for storing diagnostic data such as, for example, metabolic-related clinical data. The computer microprocessors can be processors that are typically found in personal desktop computers (e.g., Windows, Mac, or Linux based operating system), portable computers, mainframes, minicomputers, or other computing devices. In one embodiment, the networked client/server architecture provides a classic three tier client server model: $1^{st}$ tier—Database Server, $2^{nd}$ tier—Application Server, and $3^{rd}$ tier—Client(s). In one embodiment, a relational database management system (RDMS) provides the interface to the database either as part of the Application Server component or as a separate component (RDB machine).

In the database-centric client/server architecture, the client application generally requests data and data-related services from the application server which makes requests to the database server. The server(s) (e.g., either as part of the application server machine or a separate RDB/relational database machine) responds to the client's requests and provides secured access to shared data. Data may be also sent to the database server or captured by the database server which can be stored in the database and also provided to requesting clients.

Client

The client components are complete, stand-alone personal computers offering a full range of hardware and software features to run applications. The client component operates under any operating system and includes a microprocessor (μ-processor), communication means (I/O), storage means (memory), and a user interface comprising input and output means. The user enters input commands into the processor through input means which could comprise a keyboard, mouse, touchscreen, trackball, touchpad, or a combination thereafter. Alternatively, the input means could comprise any device used to transfer information or commands. The output means could comprises a display, such as a computer monitor, a television, LCD, LED, or any other means to convey information to the user, such as a printer, sound, etc. In one embodiment, the user interface is a graphical user interface (GUI) provided on a display and which is written and operating under the Java programming language (Sun Microsystems) as a Java compatible browser or Java Virtual Machine (JVM). The GUI provides flexible navigational tools operable by the input means to explore patterns in the relationships between various aspects of the clinical data. For example, in one embodiment, the GUI permits a user to visualize and explore relationships using Enhanced File Management (i.e., tree structures of related files, i.e., members of a same study or group, same-tagged files, etc). The clients and the Application Server communicate via Java's RMI (Remote Method Invocation).

Server

The server component(s) can be a personal computer, a minicomputer, or a mainframe and offers data management, information sharing between clients, network administration and security. The Database Server (RDBMS—Relational Database Management System) and the Application Server may be the same machine or different hosts if desired. In one embodiment, the Application Server is preferably a Java application (JDK or JRE) running on a supported UNIX platform (e.g., Linux, Irix, Solaris). The Database Server in one embodiment is preferably SQL-capable (e.g., MYSQL, Oracle). In one embodiment, the Application Server and Database Server communicate via the protocol implied by the JDBC (Java Database Connectivity) driver of the RDBMS. The Application Server preferably completely isolates the client from any notion of relational databases; the client's view is one of (Java) objects, not relations. The present disclosure also envisions other computing arrangements for the client and server(s) in other embodiments, including processing on a single machine such as a personal computer as standalone tool, a mainframe, a collection of machines, or other suitable means.

Client/Server Communications

The client and server machines work together to accomplish the processing of the embodiments of the present disclosure. The preferable protocol between the client and server in one embodiment is RMI (Remote Method Invocation for Java-to-Java communications across Virtual Machines). RMI is a standard defined by the Java Core. The isolation of clients from each other requires that each client gets its own server instance as a container of all client related data like database connection or query status. A root server allows connection bootstrapping by creating server instances. The resulting communication model with all three tiers is depicted in FIG. 1.

Database Hardware

The database is connected to the database server component and can be any device which will hold data. For example, the database can consist of any type of magnetic or optical storing device for a computer (e.g., CDROM, internal hard drive, tape drive). The database can be located remote to the server component (with access via modem or leased line) or locally to the server component. In another embodiment, a single processor on which both the computer program disclosed hereafter and the database can be provided.

Database Format (Relational)

Figure 2:
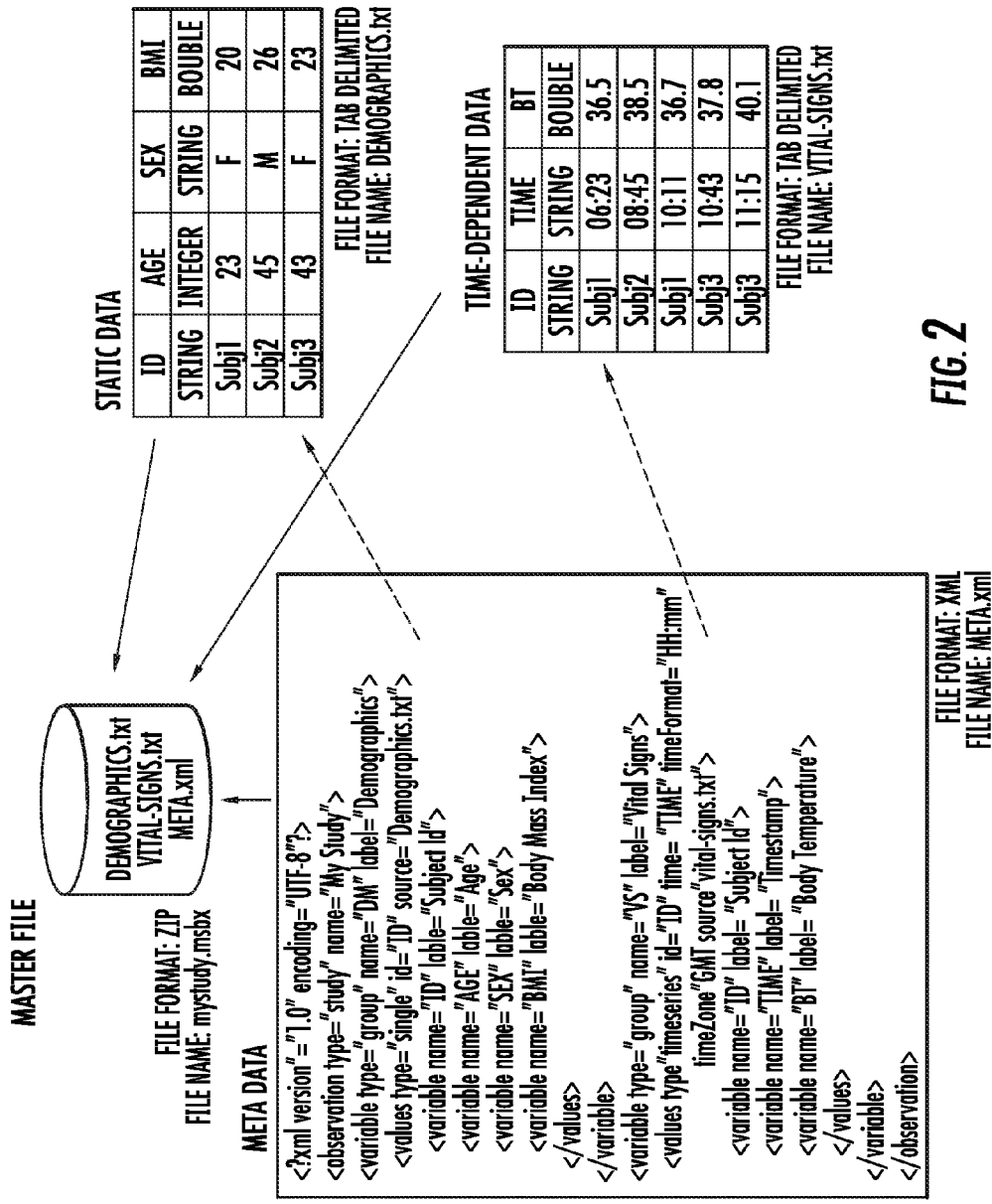
FIG. 2 depicts a data file provided by a database according to the present disclosure.

The data format used by the underlying data handling and visualization engine of the present disclosure, which are discussed hereafter in later sections, is a simple yet powerful format to store observations about subjects. In particular, the database in one embodiment is a relational database created/derived from existing clinical data sets and/or databases (demographics, OGTT data, meal data, Lab data, etc.) that is organized and accessed according to relationships between data items. In one embodiment, the database is SQL compatible with standard JDBC supported mechanisms and data types. As mentioned above, the relational database would provide a plurality tables (entities). The rows of a table represent records (collections of information about separate items) and the columns represent fields (particular attributes of a record). In its simplest conception, the relational database is a collection of data entries that "relate" to each other through at least one common field. For example, FIG. 2 shows a simple example of a study provided in a master file named mystudy.msbx comprising two files demographics.txt and vital-signs.txt and a metadata template meta.xml. In this example, the demographics.txt file contains demographic information (static) provided in a format for tabular data exchange, such as TAB or comma delimited text, and the signs.txt file contains the measurements of one parameter (body temperature) over time also provided in a similar format. As shown, the metadata template pulls data from the other two files, and all the files may be packaged together in a ZIP-compressed archive in one embodiment.

With this database format, observations can be done either once and be static (without a reference to time), or they can be performed multiple times and be time-referenced. Observations are described by variables. Variables can be organized into thematically related groups (sometimes called domains). Each group of variables is represented in the form of a table. Each row in the table corresponds to an observation about a subject. Each column corresponds to a variable describing the observation. There can be any number of tables. Further meta-information describing the organization and labeling of tables and variables, is defined in a separate metadata file, called a session file. In one embodiment, the session file is provided with the extension .mmi in which all user-generated data associated with one or more .msbx files is saved. For example, the .mmi file can contain a series of user-specified annotations, such as an edited title, an associated text note, one or more associated Tags, etc. An .mmi file can be created, modified and resaved, whereas in one embodiment a .msbx file is static and not modifiable by the computer program (i.e. program 150). In this embodiment, the computer program 150 facilitates the creation of a user-generated metadata file (i.e., the session file) that points to information without corrupting the source data. In particular, the session file can only be used in combination with the source data as containing only pointers to the source data, without which the pointers are effectively meaningless. Thus, the session file acts as a guide to the source data's classification and interpretation without altering the source data in any way. In such an embodiment, if the user tries to open a session file without the program 150 having access to the source data, the program will prompt an error and halt loading the session file. If the associated source data is available for accessing, the program 150 will launch both the session file and the source data for combined viewing and manipulation in the software environment. However, if source data preservation is less stringent, then it is to be appreciated that the computer program 150 in another embodiment can be implemented to add metadata to the source data file without corrupting the source data such that both are contained within the same file.

In still another embodiment, a second type of file can also be created by the computer program having the extension .mmg which contains all user metadata associated with a single Group as opposed to an entire session saved by the session file in which multiple Groups may be present. It is to be appreciated that neither a .mmi or .mmg file can be viewed without loading the corresponding .msbx file(s) because the metadata of these user-generated files has no meaning without the original data contained within the .msbx file(s).

II. Data Flow Process

Figure 3:
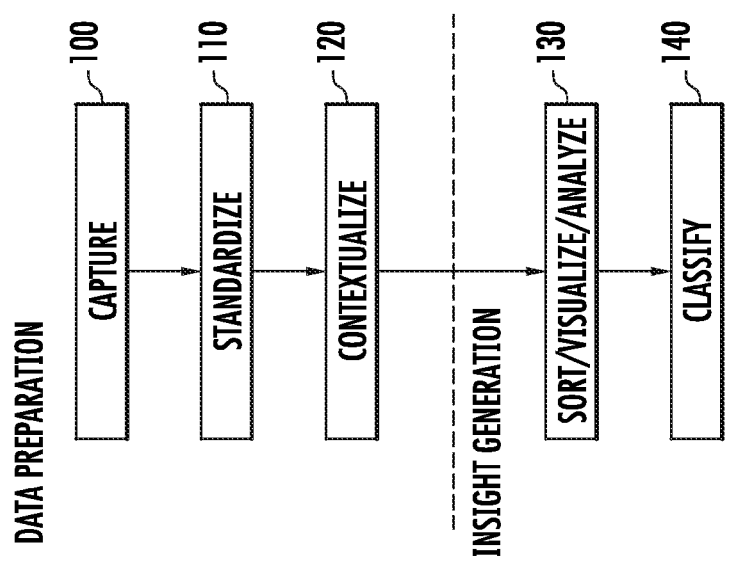
FIG. 3 depicts an overview of a data flow process from data preparation to insight generation according to the present disclosure.

An overview of a data flow process for insight generation according to an embodiment of the present disclosure is depicted by FIG. 3. It is to be appreciated that using the system depicted by FIG. 1, a plurality of patient identifications having associated therewith the patient data objects or data can be captured in step 100 from different data sources, such as data files produced during clinical studies, or extracted from personal blood glucose measurement devices, manual inputs, such as typing in data on an input device, glucose values formatted in standard electronic file formats such as Excel, .csv, ASCII, binary, etc., or any other types of diagnostic data (other than glucose) from nonclinical study sources.

In one preferred embodiment, the captured patient data objects is patient diagnostic or physiological data, such as time-series glucose data, collected from a glucose monitoring device (spot, continuous, or both) along with the associated information collected therewith and provided to the RDBMS server. For example, such data can be captured from a number of clinical studies, like a study to determine differences in postprandial glucose signals after different types of meals in patients with diabetes, a study examining the impact of physical exercise on glucose levels in patients with diabetes, a study evaluating the quality of continuously recorded changes in glucose concentration in blood and in interstitial fluid during hypo- and hyperglycaemic phases under clinical-experimental and on quasi everyday life conditions in patients with diabetes, or a study examining tissue glucose traces in healthy subjects during daily life conditions and after different meals. In another embodiment, a computer "kiosk" can be provided in which to upload data from CGM devices, SMBG meters and insulin pumps. In another embodiment, patient device data can be uploaded from remote sources, i.e., via the Internet; and information also pushed from the computer program back to the patient device through the Internet.

A data compiler, such as for example provided by the RDBMS server, may then standardized such captured data in step 110 by transforming the data into a file format such as depicted by FIG. 2, e.g., placing static and variable data in relational tables, imposing standardized vocabulary for comparable variables, and attaching variable metadata to enrich the capture data. In one embodiment, for data handling the StudyBrowser library available from Macrofocus GmbH (Zurich, Switzerland) is used. The data format provided by the StudyBrowser library is a well-documented table based format that can be generated by the use of most common data analysis software packages such as Excel, Matlab, or SAS. The data format of the present disclosure extends the Study-Browser format on which it is based with additional information that is required to support software components of the present disclosure which are discussed hereafter in a later section. The additional information provided by the data format of the present disclosure includes identifiers for software-specific data categories such as metabolic dynamics indicators or reference data. This additional metadata is stored in an XML-based metadata file, such as depicted by FIG. 2.

A user then in step 120 may contextualize selected relevant variables and add disease-specific metadata using the GUI as described hereinafter in later sections on a client computer (e.g. client computer depicted in FIG. 1). In step 130, the user may then explore and compare patients' diagnostic information, identify relationships between variables and metabolic indicators, and identify patterns of similarities and difference among events, patients, and population by sorting, visualizing, and analyzing Data Memos, which are explained hereafter also in a later section. This sorting, visualizing, and analyzing of Data Memos is further enhanced by lastly the user in step 140 classify them via assigning user defined Tags and grouping observations in Groups such that disease classifications and hypothesis are created that are sharable among the related disease management community. It is to be appreciated that the user can add one or more user defined Tags to any patient data object for data interpretation and findability as is explained in later sections. In one embodiment, one or more Tags can be assigned to a patient data object at the level of the Subject (global characteristic), at the level of the Data Memo (data associated with the subject, but not global to the subject), or both. For example, a series of tags can effectively map a series of traits, characteristics, observations, symptoms or other descriptive criteria that are used in the practice of medicine to qualify a medical condition, such as the symptoms that lead to the diagnosis of disease.

In another use of the computer program 150, the user can generated a report to show a patient how they currently compare to their own past, or to members of a comparable patient population (i.e., comparing an individual's data against a population average or outliers). Such a report may also provide summary statistics based on analysis of diagnostic information; and may also reveal the cause and effect of certain observed physiological trends, such as hyperglycemia after a meal. The production of such reports (with value for the individual patient) can also occur in combination with medical research, such as insights created through the hierarchical classification and descriptive tagging of a larger patient population in which the patient is but one individual. Additionally, for example, the use of the computer program according to the present disclosure for research may lead to the establishment of new diagnostic algorithms according to patterns which emerge from classifying and describing information that is observed in a database of patient diagnostic records. The use of computer program according to the present disclosure for evidence-based medicine offers new and improved methods for interpreting large, multi-variant datasets of time-series diagnostic information.

It is to be appreciated that the above mentioned processes are facilitated by a computer program according to the present having software components which permit a user to find meaningful patterns and relationships within diagnostic data. This benefit is achieved through a unique combination of: (1) a user-defined, editable filing structure into which Data Memos may be organized, analogous to a taxon for biological species (hereafter referred to as "Groups"); and (2) user-defined keywords that are used to describe the data (hereafter referred to as "Tags"). Because the user may not know in advance how to classify data, the computer program according to the present disclosure enables data classifications to be easily editable and is designed for iteration which is facilitated by the .mmi file—that references the sources data (.msbx files) without altering or corrupting the source data. Therefore, it is always possible to return to a clean slate and there is no disincentive to iterate when multiple session files can be saved as competing alternatives to a research hypothesis. Knowledge about how to classify the data is gained through use of the computer program in combination with data. It is to be appreciated that the computer program according to the present disclosure provides a structured approach to classification, but does not describe a set of strict rules by which data should be classified. Instead, with the computer program, the user can define and test their own logic and system of classification for diagnostic data. Through the use of the computer program according to the present disclosure, one or more accepted systems for diagnostic data and patient classification will emerge for discussion within the scientific community.

For the purposes of this invention disclosure, a Data Memo is defined as one or more series of data associated with a patient. It is to be appreciated that a Data Memo does not include all of the information of its associated patient provided in the source data, but only a subset thereof. For example, a Data Memo can include time-series measurements, demographics, lab values and any other information associated with a patient, such as a participant in a clinical study. To be clear, a Data Memo may contain "one or more series of data" but the time stamp (start and end point) is the same for all data, that is either the same or contained within the time period defined by the start and end point. In other words, all sets of data associated with a Data Memo share the same time reference within the overall timeline of the Data Memo. A Data Memo cannot contain data that starts before it's defined start point or after its defined end point.

A Data Memo can be placed into a Group. Said differently, Groups are containers for Data Memos, and thus refers to custom sets of study subjects and/or data segments. Providing such a grouping function in the computer program allows the user to create and manage personalized data folders i.e., Groups, for targeted examination and analysis. Although data from multiple studies can be combined in custom Groups, a Data Memo can only exist in one Group at any time, or in other words, a specific Data Memo is a unique data object. Copies of a Data Memo can be made and placed into more than one Group at a time, but each copy of the data is treated as a unique Data Memo. In other words, a unique Data Memo cannot exist in more than one Group at a time. The purpose of having unique Data Memos is to allow a researcher to explore multiple hypothesis for the same data (using Data Memo copies) but without confusing the uniqueness of each Data Memo within the experiment. For example, once a prevailing interpretation or theory is established for the data in question, copies can be placed into a "back-up Group" or deleted altogether, which is also an example of the process by which a session file is iterated.

A Data Memo can be labeled with one or more Tags. Said differently, Tags describe a Data Memo (and the same Tag may be used to describe multiple, different Data Memos). A Data Memo can have an unlimited number of Tags. Copies of data can also have the same or different Tags as the original Data Memo.

Groups can be organized in a flat and/or hierarchical file structure. Groups that are hierarchically organized may be visualized in a Select Table feature of the GUI of the computer program as an indented data structure, and Tags can also be viewed in association with the Data Memos in this hierarchical Group structure so that the user can visualize where certain Tags or series of Tags occur within the hierarchy. In this way, the entire organization of data can be seen in a structural overview on the GUI. This visualization technique aids the user to locate and/or classify Data Memos by revealing the organization of Groups, Data Memos and Tags.

Comparisons of data in Groups and data with Tags can be easily performed using the Union feature, which pools all members of the selected Groups and all members with the selected Tags into a single selection without changing the placement of data within the Group and Tag hierarchy. The technical term for the Union operation in computer science is a logical OR. Comparisons of data in Groups and data with Tags can be similarly performed using the Intersect feature, which enables a person to use one or more selected Tags as a filter on the members of one or more selected Groups. Tags can be used to Intersect Groups, but Groups cannot be used to Intersect Groups or Tags. The technical term for the Intersect operation in computer science is a logical AND. Tag names can be edited by the user at any time. All Data Memos carrying the edited Tag will reflect the updated name. Group names and color assignments can also be edited at any time. Members of the edited Group will reflect the edits, i.e., adopt the new color of their Group assignment.

The insertion, removal or relocation of Data Memos into the Group hierarchy does not impact on the placement, tagging or naming of existing data. Color will change according to the Group assignment (following the rule that Data Memos inherit the color of their Group). The reorganization of a Group within a hierarchical or flat structure will carry its associated Data Memos without affecting Data Memos inside of other groups.

Embodiments of the present disclosure are designed to create and handle specific time-based segments of patient data, i.e. the user created Data Memo, wherein users, such as researchers, may use the features of the present disclosures to define one or more temporal sequences of data that they wish to explore. As the Data Memo is a time-series data segment, e.g., a temporal subset of all patient data objects associated with the subject identified by a patient identification in the source data that occurs within a user designated time period, such as insulin, glucose, meals, medication, etc., as well as all non-temporal information associated with its parent file, such as age, gender, etc., by focusing on the data associated with a specific time-period, Data Memos enable a user to conduct event-based exploration of diagnostic information provided in the inputted source data. The importance of focusing on "events" in time-series diagnostic data, particularly metabolic data, is that a person's life comprises a real-world series of occurrences: sleeping, waking, breakfast, lunch, sports, dinner, snacking, and so forth. Therefore, understanding the significance of diagnostic information highlights the need for knowledge about its temporal context. It is to be appreciated that many diagnostic parameters vary significantly according to the time of day and the patient's behavior. Therefore, it is also crucial to know the measurement time and ideally, the surrounding events, in order to properly interpret the significance of the measured parameter. The same can be said of the importance of knowing the device that was used to make the measurement because not all diagnostic devices record comparable values.

A humanist approach to interpreting diagnostic information is especially important for understanding lifestyle-related disorders such as diabetes. The daily life of a patient is not an arbitrary, 24-hour or 7-day modal period, but demarcated with hourly decisions and actions that directly shape a person's unique metabolic constitution. Understanding the subtleties of a patient's life and choices cannot be entirely understood in average view; and neither can optimal therapy be prescribed for an individual in a general "one-size-fits-all" manner. Therefore, the Data Memo offers a researcher the ability to focus on specific time periods of interest and events; and also provides statistical-analytical tools to quantify these specific time-based episodes once they have been identified.

Data Memo comparisons can be made for a single patient or a group of patients across an entire patient population. Data Memos may also accommodate and store many forms of user-added information and preferences such as, for example, user-defined Layers and their associated content, including but not limited to: text, images, tags, diagnostic measurements, nutritional data, GPS tracking, motion recordings and dose information for medications. It is to be appreciated that adding a Custom Event is the mechanism by which this additional information is assigned. Note, the interface by which a Custom Event is created is via using a Custom Event editor in the Layers Panel, which is then assigned to a Data Memo's timeline in the Visualize workspace. A Custom Event also contains an information panel that can be edited with text and photographs relevant to the event. The user can also create a text note or assign one or more tags to accomplish a similar goal. However, the advantage of a Custom Event is that it places an event marker on the timeline of the Data Memo as well as providing a reference panel for inputting descriptions of the event, such as text and photographs.

In one specific embodiment, the computer program can be used for the orderly classification of patients and their data into taxonomy of appropriate categories, wherein "appropriateness" is determined by a medical professional, for the purposes of diagnosing various conditions and identifying natural relationships in the progression of metabolic health and disease. In this respect, the computer program enables a user to leverage a database of clinical information about a population to establish meaningful patterns in the data against which single or subgroups of patients can be referenced. A medical professional can use the computer program according to the present disclosure to classify patient data according to perceived similarities and differences; and to compare individual data against population trends. Using the Data Memo function to focus on specific events in a patient's overall data profile, medical professionals can make focused comparisons of meal response, nocturnal metabolism, athletic performance and so forth. For example, provided hereafter is an example of the usefulness of Data Memos in medical research.

The researcher selects data for a population of patients with the intention to understand how dinner affects their overnight glucose control. In order to isolate the event "dinner" from within the patient data, the researcher creates a series of Data Memos with the common start period of 5 pm and common end period of 10 pm and places these Data Memo files in a Group called "Dinner." Next, using data from the subsequent overnight for the same patient population, the researcher creates Data Memos with the common start time of 10 pm and common end time of 6 am. The researcher places these newly created Data Memos in a Group called "Overnight." The researcher then selects all of the Data Memos in the Group "Dinner" and sorts them (in the Select Table) by Area Under the Curve, a metric that represents the magnitude of glucose exposure. For all Data Memos that fit her criteria for an elevated AUC value, the researcher assigns a Tag called "elevated." She repeats the same procedure for the Data Memos in the Group "Overnight," using an appropriate cut-off value to identify data with elevated AUC, and she assigns the Tag "elevated" where indicated. Finally, she selects all members of both Groups, "Dinner" and "Overnight," and intersects them with the Tag "elevated" by using a Boolean query with the logical AND operator. The results of this query show her which patients are elevated in both instances, as well as those patients who suffer overnight hyperglycemia despite a well-controlled response to the dinner meal. Using this intelligent selection, she can deepen her investigation into possible causes and therapeutic actions.

Interactive features of the computer program according to the present disclosure enable a medical professional to explore the meaning of data, create better systems of disease classification and patient diagnosis, and discover new insights into human health and disease. The major software components, objects, and features of a computer program 150 according to the present disclosure are discussed hereafter with reference made to FIG. 4.

III. Software Components, Objects, and Features

Data Compiler

The Data Compiler 155 in one embodiment is implemented with the computer program 150 of the present disclosure, but in other embodiment may be provided as a stand-alone software application. The data compiler 155 guides users through a data formatting and conversion process using a simple wizard-like interface which provides assistance with generating the meta-information, and packaging all the artifacts into a single archive file. Data formatting is the process by which raw, archived data from a clinical study is converted into a file format that the computer program can read. As mentioned above in a previous section, the file format of the present disclosure is based on simple tables that contain both static and time-dependent data. Formatting these tables involves labeling to indicate what type of data they contain, such as time-series glucose, patient demographic information, or various other meta-information. The design of a clinical study must also be specified through the process of data formatting (i.e., quantity, sequence and purpose of measurement sessions, members of patient sub-groups, etc). Without this step, data from a clinical study can be loaded by the data loader 160, but such data will not benefit from the full features of the computer program 150. In other embodiments, the file format of the present disclosure can be created with simple tools such as Excel or text editors using human-readable text.

In one embodiment, raw data in the form of CSV (Comma Separated Values) formatted tables and other such formats (e.g. SDTM) can be used. During the conversion process, the Data Compiler 155 presents users with a summary of the available data. Users then provide naming and other contextual information, specifying the names and locations of the metabolic dynamics indicators, reference data, etc. The output of the data formatting process of Data Compiler 155 is a single file that conforms to the file format used by the computer program 150, i.e., .msbx file (FIG. 2) that contains all the data and can be loaded by a data loader 160 of the computer program 150.

Data Loader

The Data Loader 160 is used to import and map source data in the .msbx file format. Other features of the data loader are discussed hereafter in a graphical user interface section in reference to a Source column.

Pathway Reporter

It is to be appreciated that the computer program 150 provides a series of tools (i.e., software components) that can be applied to data for the purposes of inventing new methods of interpretation. Importantly, if a successful method is discovered using the computer program 150, the method should be recorded and shared with other researchers; and potentially developed into a packaged product. Therefore, the computer program provides a function, called Pathway Reporter 165, which traces what steps are taken to apply visualization methods and analytics.

The Pathway Reporter 165 will document a user's process in two ways: automatically record the system state at well-defined points of change; and allow users to explicitly mark, annotate and save the system state at any time. The computer program 150 will automatically have the processor take a snapshot of the complete system state when a change occurs and the change will be added to a history of events that the processor stores in memory. In response to a user input command, the processor will display on the display a display box which allows the user to access and navigate the history of events, explore diverging paths of exploration at important branch points, and document the process of a discovery.

Data Memo

As mentioned above, the Data Memo 170 is a fundamental object represented and manipulated by the computer program 150. The Data Memo 170 is a copy of the source data that has a user-defined start time and end time which may be the same as the start and end time of the source data, or may be some interval in between (e.g., glucose time series data from clinical study datasets) and which can include direct user annotations while preserving the integrity of source data. Data Memos can accommodate and store many forms of user-added information and preferences such as a custom Title, Tags, Notes and Custom Events. The purpose of a Data Memo is exemplified by event-based analysis, such as focusing in on a time period that encompasses a single event in the source data, such as a meal. A single source data file may be used as the basis for creating a multitude of Data Memos, each representing one or more events that the investigator would like to analyze in detail. A second important feature of the Data Memo is that is supports the creation of user-defined metadata, such as Title, Tags, Notes and Custom Events, which are used to aid in the data's interpretation without corrupting source data to which it refers. Metadata forms a "layer" that does not corrupt the original data. This allows the researcher to easily create and edit metadata and entertain multiple, competing interpretations of the data's significance. Metadata is saved in the .mmi file format and points to the source data contained within .msbx files. The .msbx files are never altered by the program.

Segment

A segment 175 is a variant of the Data Memo 170 which stores a user-defined subset of a patient's glucose time series, as opposed to a full copy of the original source patient time series trace. Segments 175 are intended for event-based analysis.

Group

A group 180 is a custom set of Data Memos 170. The Group 180 allows the user to create and manage personalized data folders based on clinical study sources for targeted examination and analysis. Data from multiple studies can be combined in custom groups. Groups 180 can be nested and structured into hierarchies for use as experiment frameworks or for the creation of classification systems.

Tag

A Tag 185 comprises one or more descriptive keywords that can be associated with each Data Memos 170. Users can freely choose and manage the keywords on the Tags 185 to annotate and classify objects. Tag assignment to objects of interest can greatly increase the user's capacity to recognize and discover related information types emerging over the course of investigation.

Representation

A Representation 190 is an analytical visualization method. Segments or whole datasets can be rapidly toggled between representation modes to cross-compare apparent insights or to refute incidental artifacts of a specific representation. Example of such representations include: (a) Time Series—Glucose over time representation, which is a "CM curve" for continuous glucose time series that serves as the reference visualization method and a starting point for observations; (b) Shape Memo which is an Area Under the Curve (AUC) representation and in which a series of measurements is displayed as a 2-dimensional geometric shape, whose boundaries are defined by a start time, end time, and a "baseline glucose threshold" (intended as an aid to event-based analysis); (c) Phase Space, which is a method to reveal the dynamic properties of a system in which a quantity changes over time; and (d) Bubble, which is a Point representation for plots, and which is the default representation for an Analyze workspace. Polar Coordinates are another method of representation; so are smoothed or averaged curves ("River diagrams.") Note that the "bubbles" in Analyze represent a subset of the original data—they plot metrics that are derived from the data, such as average, SD, mean, median, mode, AUC or any other derived calculation based on time-series data. Bubbles can also be mapped to other, non-time-series data such as HBA1c. By mapping a Bubble to multiple variables, it is possible to visualize multi-variant comparisons of the data.

Layer

A layer 195 is a user interface feature designed for optimal control over data viewing, wherein multiple data types are present in a single data memo. A user can turn visibility on or off to view multiple time-synchronized information types in combination. It is to be appreciated that each Layer maps to a category or "type" of data. For example, there is one Layer for glucose, one for insulin, one for recorded events, one for custom events and so forth. By turning on and off visibility of a Layer, the user can indicate what combination of data they wish to see in overlay. Controlling the settings of a single Layer enables the user to indicate what version of the data type they wish to see, for example, CGM glucose versus SMBG glucose (or both). It is to be appreciated that turning on or off the visibility of Layers does not affect the source data, which remains part of the Data Memo irrespective of Layer settings.

Custom Event

A Custom Event 196 is user-specified marker for an event occurrence that does not exist in the original data structure. It is to be appreciated that the clinical data can include data collected from outpatient and routine clinical practice settings as well as from clinical trails. Custom Events allow the user to add observations and context-specific information that enhance the interpretation of recorded data. A Custom Event 196 consists of a user defined name or a default name assigned by the computer program 150, a description, an optional image (such as a meal photograph), and a timestamp, which may be a single time reference or a period of time containing one or more time points. Any Custom Event 196 may be used for alignment of Data Memos 170 as will be explained in a later section, and can be shown or hidden on the timeline in the same way as recorded events for clinical data. Similar to a Tag, a Custom Event 196 can also be used to select all Data Memos that have an instance of this Custom Event. Also, a Custom Event 196 can be used to generate and assign a Tag to the Data Memo, where the Tag (by default) carries the same title as the Custom Event (although this title can be later edited at user discretion)

Workspace

A Workspace 198 is a viewing area with associated functions to support the user in carrying out distinct tasks that are thematically related, such as table sorting and navigation (Select), Layer navigation, Data Memo arrangement and visual inspection (Visualize), and plotting derived metrics or other numeric values associated with subject characteristics or one or more data Layers of a Data Memo (Analyze). As will be explained in greater details hereafter in reference to the GUI, the collective function of the workspaces of the computer program 150 is to allow the user to easily move through any combination of selected data and visualization or analysis methods. Active content is carried over and updated throughout the application, allowing the user to move efficiently through successive tasks without data loss. Discuss of the GUI in reference to FIG. 5 now follows.

IV. Graphical User Interface (GUI)

Figure 4:
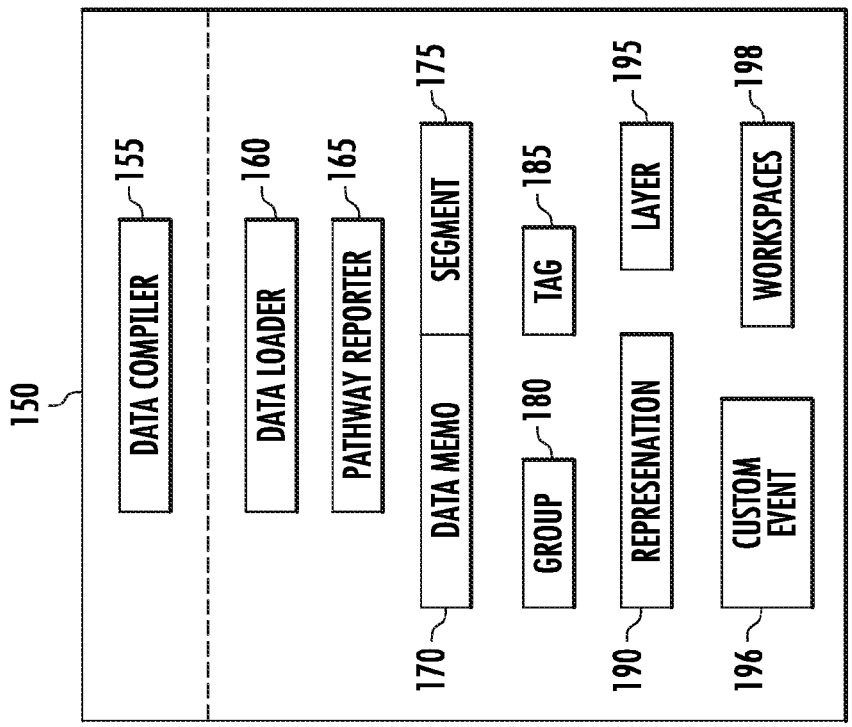
FIG. 4 depicts software components of a computer program embodiment according to the present disclosure.

The operation of the embodiments of the present disclosure will now be described with respect to a graphical user interface of the computer program which provides a user access to the above described software components, objects, and features of the computer program 150 (FIG. 4). The graphical user interface of the present disclosure allows the user to load data, save a session file (.mmi), browse the clinical studies database(s) or other data source, such as patient files that are collected in a clinical practice setting, export a Group (.mmg file), customize the visibility of Variables, define the start and end point for one or more Data Memos using the Timeline interface, create Groups, Tags and Custom Events, assign Custom Event markers to the timeline of a Data Memo, report a Pathway, export a 3rd party compatible version of the session file using Reporter, take and save a Snapshot image of the workspace(s), customize the layout and visibility of Panels, customize the column positioning of the Select Table, fix or liberate the axis of the Analyze graph, set the axis for the Analyze graph, set the Glucose Threshold for one or more Data Memos, toggle between modes of Representation (plot, Shape Memo, phase space), launch a notepad and enter or edit text, organize the structure of the Group hierarchy, perform searches, and to visualize and explore relationships e.g., tree structures of related files, e.g., members of a same study or group, same-tagged files, etc. As in most "windows" applications, each display screen of the disclosure generally comprises a window title bar, a menu bar (with command such as File, Edit, and the like), a tool bar (with options such as Close, Paste, Clear, and the like), and an information display region. The information display region may, for example, display a query window or a results window.

Figure 5:
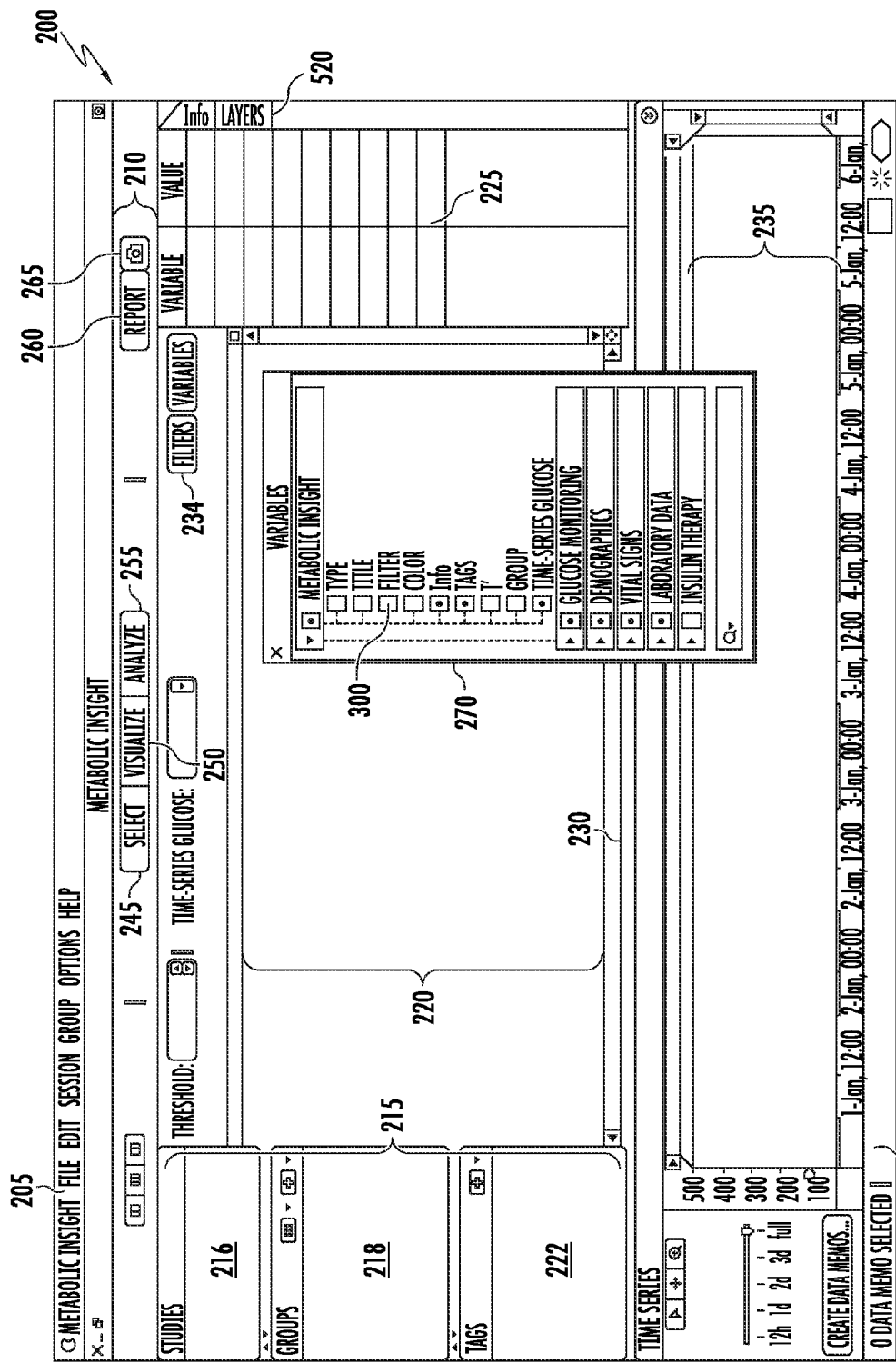
FIG. 5 depicts a graphical user interface according to an embodiment of the present disclosure which provides user access to the software components depicted by FIG. 4.

As shown by FIG. 5, a preferred embodiment of the graphical user interface (GUI) provided by the computer program 150 is shown. After executing the computer program 150 on a client computer (FIG. 1), the processor provides the GUI 200 on the provided display. The features of the GUI 200 in this embodiment include: a Menu bar 205, a Header section 210, a Source column 215, a Viewing Area 220, an Info Column 225, a Query Bar 230, a Time Series panel 235, and a Status bar 240. The Menu Bar 205 provides access to menu commands for data loading, saving options, and application preferences. The Header 210 enables a user to choose a window layout, to toggle between different views provided by Workspaces 245, 250, 255, and to access Report and Snapshot functions 260, 265 for data export.

Figure 6:
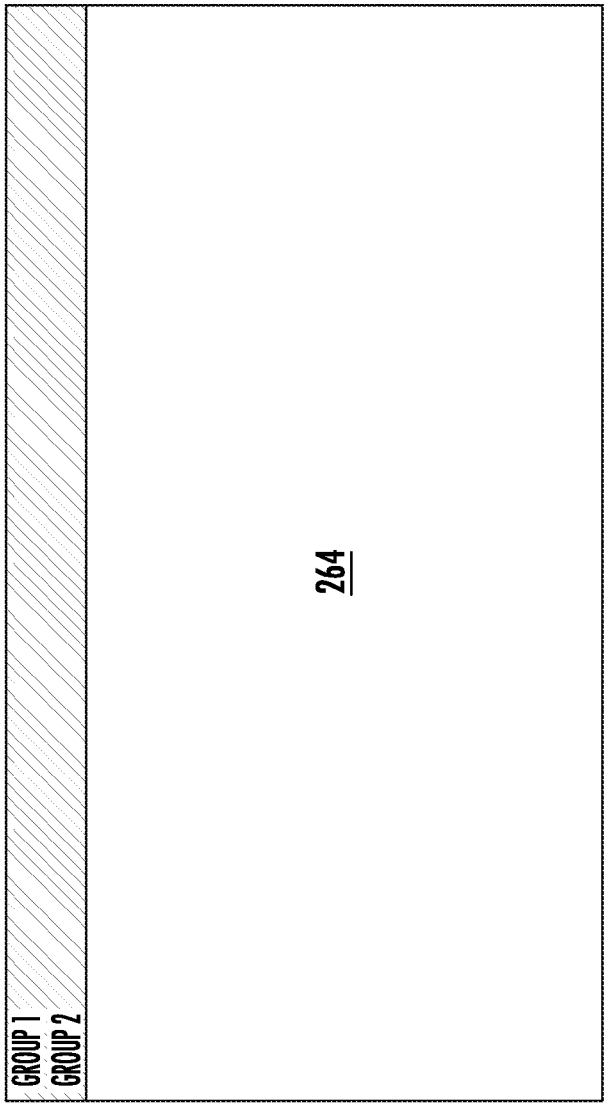
FIG. 6 depicts a report dialog panel of the graphical user interface of FIG. 5 according to an embodiment of the present disclosure.

The Report function 260 provides Pathway documentation, permits users to create reports, generate snapshots (i.e., screen captures) of the workspace(s), and output data for external use by third party software such as, for example, Excel, Matlab or SAS. Note that Reporter generates a new data file that contains a description of the user-defined Data Memos and associated metadata, including a reference to the source data file, start and stop times, Tags, Custom Event assignments, Group Assignments, Notes, etc. The report function 260 when selected will open a report dialog panel 262, such as shown by FIG. 6, which allows the user to export data in various formats for record-keeping or further analysis and validation in other tools. For data selection, the user selects from the Group list field 264, which displays all groups in the current session available for reporting. The user chooses one, several, or all groups for export in the desired format. The user Shift+click into the list to select contiguous groups, and then optionally Ctrl+click to add or remove groups from selection. Variables checkboxes 266 is used to choose which table data ("Tabular"), continuous glucose values ("Time Series"), or both, to export. The "Tabular" option exports all contents (variables) displayed in the table in the Select workspace. The "Time Series" option exports the continuous glucose time series values.

File Format checkboxes 268 are used to choose between available file formats to export data for use in other analysis tools. Examples, of some supported formats, include the following types. Text (*xml) in which data is exported as human-readable text with simple formatting. Tab delimited (*.txt, *.zip) in which data is exported as tab-delimited tables in text files with the combined files packaged as a ZIP archive. If the "Time Series" option is checked the export will include one table with the glucose time series of each group member. Excel (*.xls) in which data is exported in the native Excel file format. If the "Time Series" option is checked the export includes one worksheet with the glucose time series of each group member. Matlab (*.m) in which data is exported in the native Matlab file format. If the "Time Series" option is checked the export will include one array with the glucose time series of each group member.

The Options checkboxes 282 is used to choose which numeric values as displayed in the Select workspace ("Format values") to export, include all source clinical study data in addition to selected groups, and/or to open exported data directly in another program where applicable ("Open output file"). The "Format values" option formats numeric values (decimal places) to the same form in which they appear in the table in the Select workspace. The "Include study data" option exports all data from the source clinical study (all subjects) in addition to the selected custom groups. The "Open output file" option (when applicable) launches the application associated with the chosen file format after export. Generate button 284 is used to generate the report generation, wherein the user is prompted for a save location. In view of the above, it is to be appreciated that the computer program according to the present disclosure is creating new data and exporting it in these established file formats. The new data consists of the user-defined time points for Data Memos, the Groups and their hierarchical structure, the Tags and their assignments to Data Memos, the Custom Events and their assignments to Data Memos, the Notes and their assignments to Data Memos, Groups, Tags and Custom Events, Pathways, which are the series of user actions that are recorded by the software, and diagnostic macros (i.e., series of user-defined Tags joined by Boolean logic). Even though the computer program is creating this new information based on non-corruptible source data (e.g., the patient diagnostic files), all metadata in the exported files is unique and cannot be created any other way.

Turning back to FIG. 5, the snapshot function 265 enables a screenshot of parts of the graphical user interface to be captured by the processor as an image which can then be later exported. For example, the Snapshot function 265 allows a user to capture images of specific objects, such as tables, data memos, text notes or event panels and will include all such content which may be represented in several pages of data currently not visible on the screen of the display (from the independently viewable workspaces as well as the configurable panels). To select which parts to capture, the user clicks on checkboxes to indicate which information (e.g., workspace and/or panel) they want to capture. The captured images are sent by the processor to a holding file in memory which is then later viewable by selecting the Report function 260. Each snapshot image listed in the holding file can then be selected by the user for exporting to an image viewer, editor or presentation software (i.e., PowerPoint). Available image file formats are .jpeg and .pdf. The Snapshot function 265 enhances the computer program by allowing users to easily export specific images to a 3rd party software for designing patient data charts, educational materials and/or communication documents.

Figure 7A:
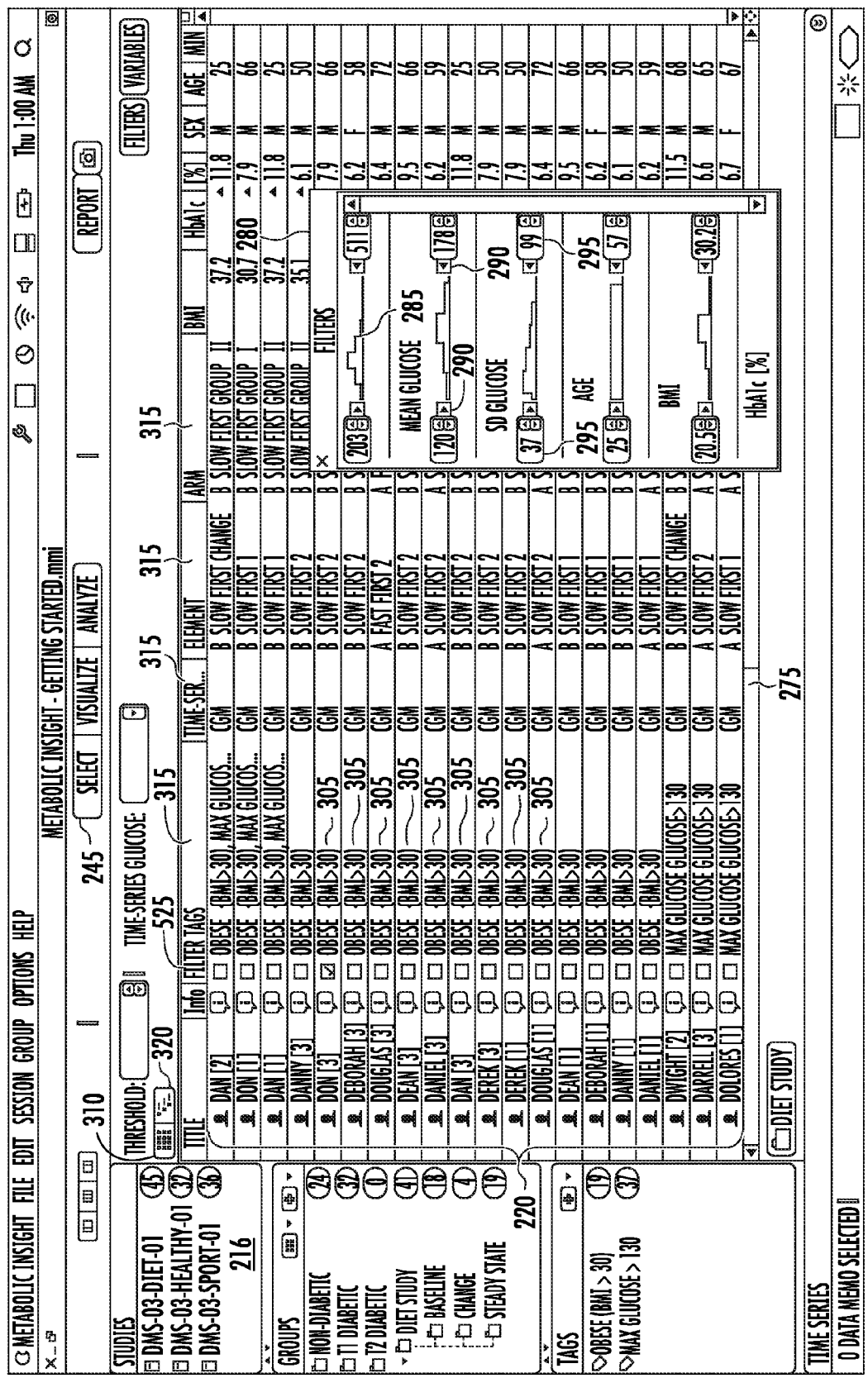

The Source column 215 enables a user to manage and organize data, such by a Studies section 216 listing source clinical studies used by the user, patient files organized by patient, or by calendar date, and Groups and Tags sections 218, 222 listing the customized Group and Tags assigned by the user to the clinic data. It is to be appreciated that after a user used a File>Open Source Data command from the Menu bar 205 and select one or more clinical study datasets for the processor to load from a local storage drive or the server into memory for use by the computer program 150, the loaded datasets will be listed in the studies section 216 of the Source column 215. For example, as illustrated by FIG. 7A, 3 datasets have been loaded, namely DMS-03-DIET-01, DMS-03-HEALTHY-01, DMS-03-SPORT01, providing 45, 32, and 36 study subject (data objects), respectively. The corresponding Study Subjects or patient data objects 305 appear in the viewing area 220.

The Viewing Area 220 enables the user to select, move, copy, delete, rename, tag, annotate, align, sort, visualize and plot objects applying Workspace-specific settings. The Info Column 225 (FIG. 5) enables the user to access object-specific information and to Manage Layers and Events, which are described in greater details in later sections hereafter. The Info Panel is a specially formatted subset of the information contained within the Select Table; and allows the user to access this data from any viewing area, i.e., Workspace. The Query Bar 230 enables the user to identify populations in the Viewing Area, and to perform logical operations on the data. The Time Series Panel 235 enables the user to reference time-synchronized glucose traces and to create segments (i.e., Data Memos) and to select Data Memos by selecting (e.g., clicking on via a mouse) their corresponding glucose trace. The Time Series panel 235 can also be used to interactively select Data Memos by clicking with the mouse on their corresponding time-series trace, i.e., glucose over time. The Status Bar 240 enables the computer program to provide application feedback to the user. The GUI 200 also provides layout options selectable via layout controls 224, 226, 228. Toggling the layout controls 224, 226, 228 alternative hid or shown the Source column 215, the Info Column 225, and the Time Series Panel 235, respectively, wherein the Viewing Area 220 expands or contracts accordingly.

As mentioned, the GUI 200 has three intercommunicating workspaces—Select 245, Visualize 250, and Analyze 255—which support the visual-statistical analysis of time series data, and specifically in one embodiment, metabolic dynamics. In particular, the workspaces 245, 250, 255 facilitate the use of the source data combined with user-generated metadata to find new insights, processes and techniques whereby diagnostic data can support medical understanding and patient treatment. The workspaces 245, 250, 255 also supports medical research involving the interpretation of diagnostic data, in terms of either: significant events in the data structure; correlations between different time points or periods of time in the data; correlations between the diagnostic data and the subject's demographic or medical history; new diagnostic algorithms involving sequential or relationship processes applied to the data and direct perception (visualization) of meaningful information that may or may not be supported by mathematics.

The collective function of the three software workspaces (Select, Visualize, Analyze) components allow the user to easily move through any combination of selected data and visualization or analysis methods. Each workspace 245, 250, 255 provides a viewing area with associated functions to support the user in carrying out distinct tasks. Active content is carried over and updated throughout the GUI 200, allowing the user to move efficiently through successive tasks without data loss. Segments or subsets of clinical data created by the user, for example, subsets of time series intended for event-based analysis, are each handled as separate data object by the computer program. As such segments or whole datasets can be rapidly "toggled" between the Workspaces 245, 250, 255 to cross-compare apparent insights; or to refute incidental artifacts of a specific representation. In addition, selecting or pointing with a user input device (e.g., mouse over) a single subject from the Viewing Area, the related subject information provided in the source data file will automatically retrieved by the processor and displayed in the Info Column 225 as well as the processor highlighting the selected subject related glucose trace among all the glucose traces shown in the Time Series panel 235. It is to be appreciated that the Time Series Panel 235 displays overlain glucose traces of all the subject or objects contained in the selected Study or Group(s), which the processor has automatically synchronized all relative to time.

Selectable variables provided in the source data are selected for display in the viewing area 220 in any Workspaces 245, 250, 255 via a variable control 232. Selecting the variable control from any Workspace opens a variable selection panel 270 (e.g., pop up control box) such as shown in FIG. 5. The variable selection panel 270 provides checkboxes by which to choose which variable are to be display by the processor in the viewing area 220. In one embodiment, the variables selection panel 270 controls the visible columns in the table provided by in the Select Workspace 245. For example, in FIG. 7A the selectable variables provided in the variable panel would be the Title, Info, Filter, Tags, Time-Series, Element, Arm, Body Mass Index, HbA1C, Sex, Age, and Min Glucose columns as well as Max Glucose, Mean Glucose, SD Glucose, and Nickname columns which are not shown but can seen via use of the bottom slider 275. In the Visualize and Analyze workspaces 250, 255, the variable selection panel 270 controls which variables should be used in the displayed plot. There are also Variables indicating the data source (i.e., the laboratory of origin), the device used to measure the data and whether the data is "trusted" by the principle investigator or data owner. These data fields provide important contextual information when working with data recorded by different people, under different circumstances, by different technical devices and in different laboratories with different, international standards for data quality and reporting. In effect, these contextual variables, although not technically patient data, are critical to conducting research with medical data that was collected by different sources and without any communication between the collecting parties.

A filter control 234 is also provided to the GUI 200 as shown by FIG. 5. The filter control 234 allows a user to command the processor to temporally exclude object from an analysis without removing or deleting the excluded objects from the current study or group. Selecting the filter control 234 from any workspace 245, 250, 255 will display a filter panel 280 such as shown by FIG. 7A. The filter panel 280 displays numeric ranges of all available variables, as well as the distribution of values across the currently selected Group or Study population in the form of histograms 285. A user can adjust the upper and lower limits of a desired value range by manually adjusting sliders 290, or by entering a value in the readout fields 295. The processor will display filtered subjects as grayed in the table provided in the Select workspace 245 and in the Time Series Panel 235. In addition, filtered subjects will not be displayed by the processor in either the Visualize or Analyze workspaces 250, 255. A user can also open the variables selection panel 270 and turn on the variable "Filter" 300 (FIG. 5), and afterwards the Filter column will be visible in the table provided in the viewing area 220 of the Select workspace. A user can then use the checkboxes in the Filter column to filter or unfiltered objects, which column may also be sorted like any other displayed column variable.

As mentioned above, FIG. 7A is a depiction of the Select workspace 245 of the GUI 200. The Select workspace 245 is used to filter and segment data, and organize the data into groups of interest. When in the Select workspace 245 of the GUI 200, patient data objects 305 listed in the Viewing Area 220 are shown provided a table view. If the patient data objects 305 are not shown as such, then the table view is selectable via a table view control 310. The table view enables sorting (ascending or descending) and filtering of displayed patient data objects 305 based on variables by clicking on the appropriate column header 315. It is to be appreciated that the column headers 315 can be customized (e.g., renamed) by the user, the placement of the columns can be rearranged, the width of the columns can be user-defined, and the type of columns displayed can be turned on/off in the variables selection panel 270. For values with established normal ranges, outliers with above- or below the normal ranges are indicated by the processor directly in the table cell via highlighting e.g. graying. The GUI 200 in the Select workspace 245 also provides a hierarchical view control 320, which enables grouping of data objects based on information type. For example, selecting the hierarchical view control 320 will display and sort the patient data objects 305 according to their associated Group tree structure, shown by FIG. 7B expanded in a Title column 325. A Menu Bar 330 is also provided to access menu commands for data loading and saving options, application preferences, and additional functions.

Figure 8:
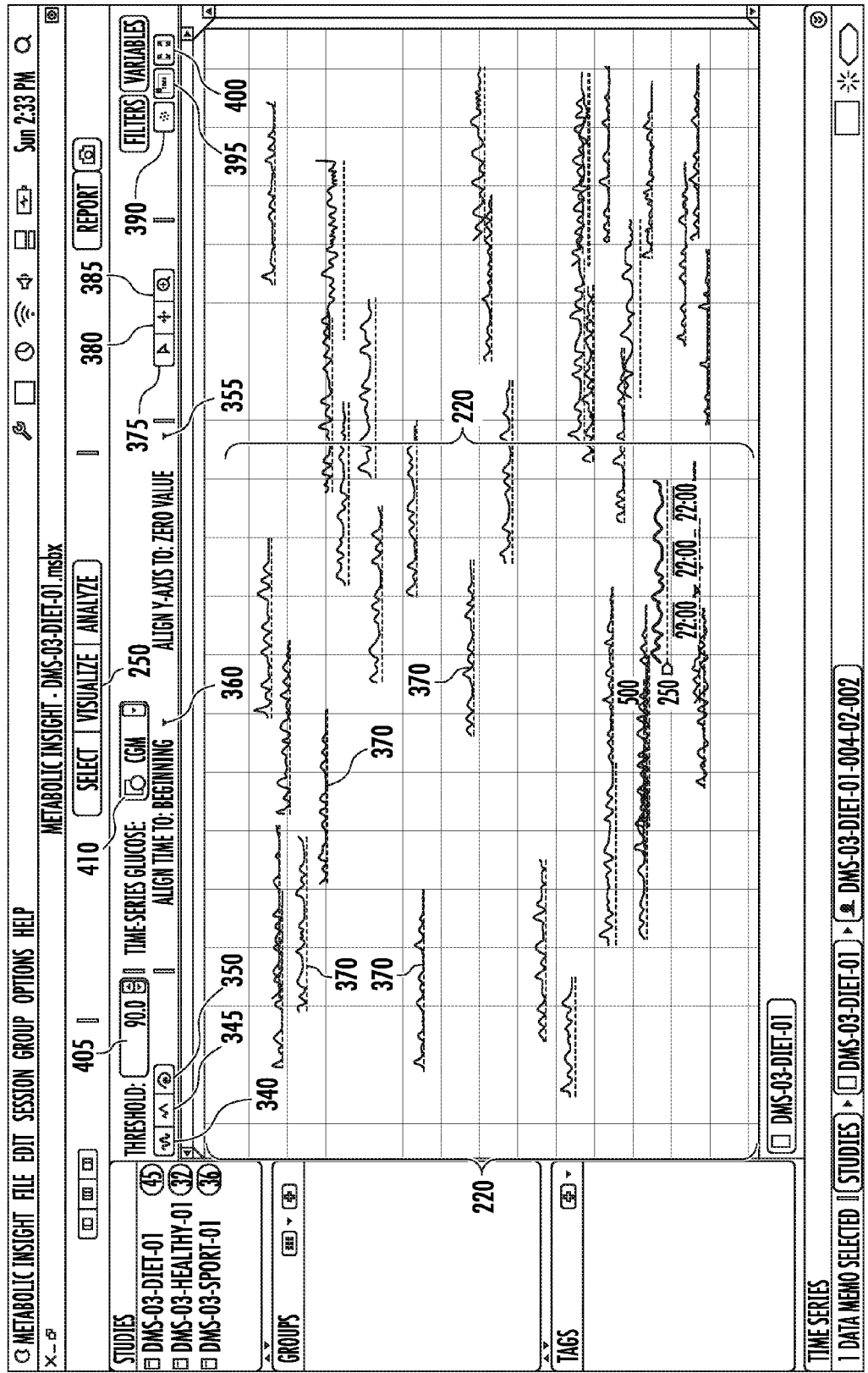
FIG. 8 depicts a visualize workspace of the graphical user interface of FIG. 5 according to an embodiment of the present disclosure and shown populated with metabolic data.

Turning now to FIG. 8, the Visualize workspace 250 of the GUI 200 is shown. The Visualize workspace 250 permits a user to explore metabolic dynamics using visualization methods, and to probe and annotate data e.g., Alignment, Target Range Analysis, Averaged Curves, Polar Coordinates, such explained hereafter in later sections. The Visualize workspace 250 works with: visualization modes, notes which are user-added text (it is to be appreciated that the user-added notes are also accessible in the Select workspace and through the Info Panel), images/photographs, sketch notations, etc., custom events, ranges, and settings. The Visualize workspace 250 also works in combination with the Layers panel, whereby visibility of certain data layers is controlled. Among these layers are: glucose, insulin, meals, custom events and any other data type that is specified as a "layer" in the .msbx file. According to the type of data that is loaded into the software, the type of layers can be customized to be appropriate for the data source. For example, if there is a layer for heart rate data, this would be then included in the Layers panel. Representation toggles 335, 340, 350 are used to toggle between Time Series, Shape Memo or Phase Space representations, respectively. As such, using the Representation toggles 335, 340, 350 a user can rapidly switch between representation modes to cross-compare apparent insights or to refute incidental artifacts of a specific representation.

Objects displayed in the viewing area 220 of the Visualize workspace 250 by default, can be freely moved around the viewing area by selecting and dragging via a mouse, wherein the processor re-positions the graphical object on the display. As such, objects can be selected, moved and overlaid onto other objects.

The user can use an "Align Y-Axes To:" option 355 to lock objects along the glucose Y axis to a selectable anchor point. In one embodiment the "Align Y-Axes To:" option 355 is selected by a drop down box which provides an align to a zero value option, which synchronizes the Y-axes of all selected objects 370 in the viewing area 220. It is to be appreciated that the above "Align" features offers a series of computer-aided alignment options that can be applied to two or more selected Data Memos. This facilitates rapid layout of multiple Data Memos according to a logic of the user's choosing from within a series of options such as align to start time, align to end time, align to relative time, align to calendar time, align to peak glucose, etc. Other features include a Minimum value option, a Maximum value option, and Mean value option, which align selected objects 370 to such statistically defined point in the glucose traces. The user can also use an "Align Time To:" option 360 to align the traces to a time value. The selectable options in one embodiment for the "Align Time To:" option 360 are: Relative time, which synchronizes selected objects to their timestamp of origin respecting study design; Modal day, which synchronizes selected objects to common 24-hour period; First Event, which aligns selected objects to the first Event (recorded or custom) present in the objects; Peak Value, which align selected objects to the maximum glucose point; and Beginning/End/Center options, which align selected objects according to their trace duration (length), irrespective of relative time.

The user may also use a manual toolset providing a select control 375 to select and move objects around the viewing area 220, a Pan control 380 to pan across the viewing area 220, and a Zoom control 385 to zoom into or out of the viewing area 220. In addition, a user can area-select a portion of the view area canvas by click-dragging with the Selection tool presented by the processor if the select control 375 has be selected by the user. To Select None, a user clicks and drags a cursor presented by the processor on the display to an empty area of the viewing area, or uses a context menu (right-click). The user may also use an Arrange control 390 to have the processor automatically arrange multiple objects in an orderly fashion in the viewing area 220, a Fit control 395 to have the processor automatically fit to screen one or more selected objects in the viewing area 220, and a See control 400 to have the processor automatically display all objects currently occupying the viewing area via zooming out the viewing area 220.

It is to be appreciated that data objects in all forms (text or representation) have 4 states: Default (unselected and neutral), Selected (active—usually selected by direct click), Probed (mouse Over or hover state; allows temporary examination of an object without selecting and includes a "tool tip" with the Nickname of the object so that it can be identified without direct selection), and Filtered (temporarily disabled from selection or analysis). In addition, multiple selections are possible in all viewing areas as well as the Time Series Panel 235 for most actions. The conventions used for multiple selections are familiar to most PC users: Shift+click to select a contiguous range of objects; Ctrl+click to add/remove objects from a selection; and Ctrl+A selects all.

A user can also adjust a threshold setting. The threshold setting indicates a baseline used for calculation of derived values such as AUC variants and bG risk indices, or any other indices that rely on an established threshold for their calculation. Note that AUC, by definition, uses a threshold of T=0. Only the variants of AUC have variable threshold settings that must be defined by the user. The threshold settings can be referenced and modified for single or multiple Data Memos from all Workspaces 245, 250, 255 using a Threshold control 405. In another one embodiment, the user can manually adjust an object's threshold by repositioning its marker or by enter a value into a readout field that appears when the cursor is placed in the glucose axis. Similar, in one embodiment a user can select the source of the Time-series Glucose, either continuous glucose monitoring (CGM) values, or a reference blood glucose values, via a Time-series Glucose selection control 410. In another embodiment, the user can select the source of Time-series data based on other time series data, such as measured insulin, for example.

Figure 9:
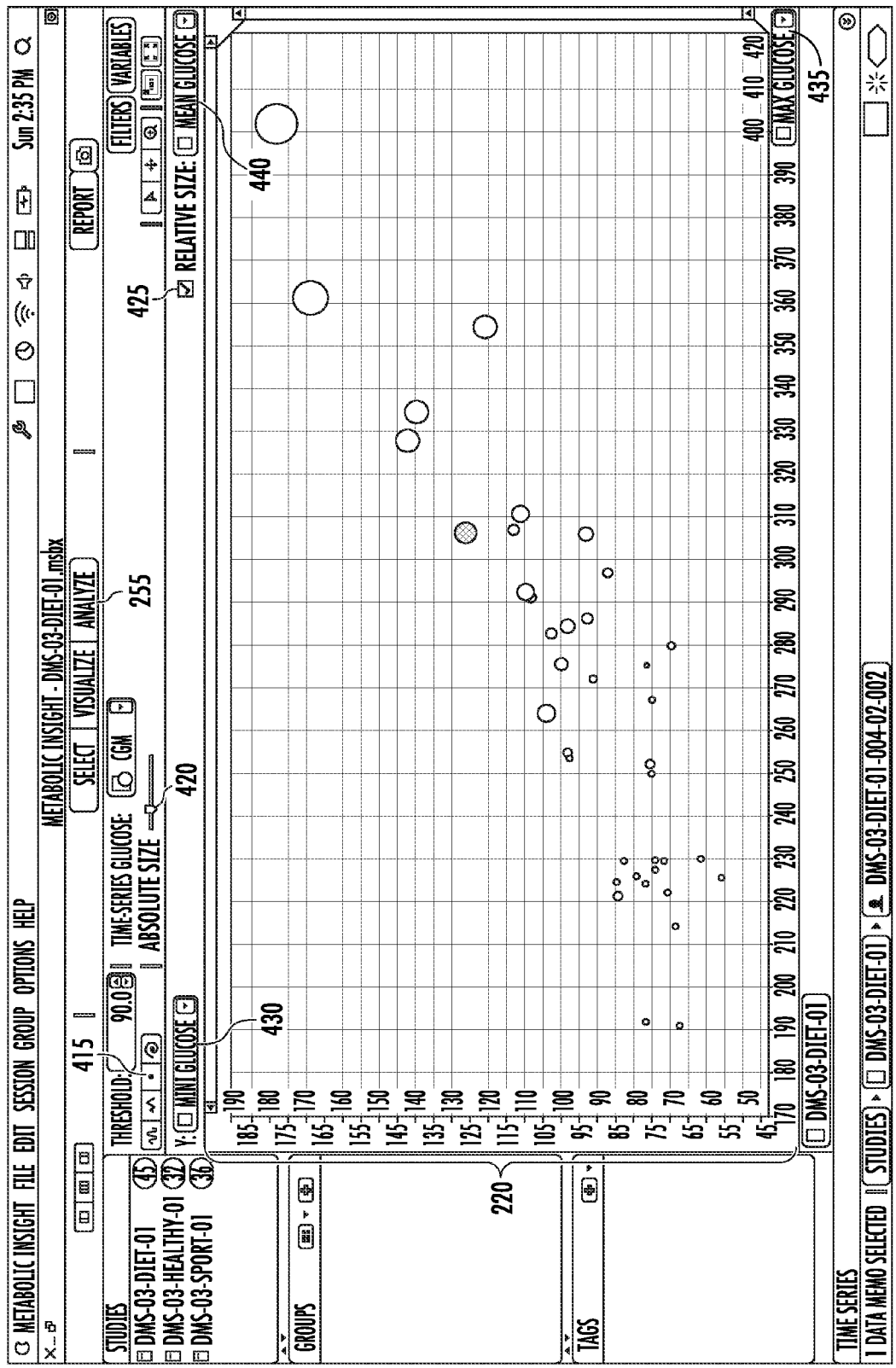
FIG. 9 depicts a analyze workspace of the graphical user interface of FIG. 5 according to an embodiment of the present disclosure and shown populated with metabolic data.

FIG. 9 is a depiction of the Analyze workspace 255 of the GUI 200. As all the same features discussed with regards to visualize workspace 250 shown in FIG. 8 are also available in the Analyze workspace 255 only the differences are discussed hereafter. The Analyze workspace 255 permits a user to explore relationships, such as for example, by viewing numeric relationships, and statistically analyze and compare derived values displayed in the viewing area 220. The default view is a bubble representation as depicted, which is also selectable via a Bubble toggle 415 as well as other representation via toggles 335, 340, 345 (FIG. 8). An absolute control 420 is provided to permit the user to select absolute size of displayed bubbles such that all the data objects may be viewed in the viewing area 220. It is to be appreciated that the viewing area 220 of the Analyze workspace 255 is a coordinate space in which the values for any two data variables can be graphed as a scatter plot.

An optional third data variable can be mapped to the data points by selecting a Relative Size option 425. Variables can be set to either the X- or Y-axis via a drop-down list 430, 435 associated with the X- or Y-axis legends. The same drop-down list 430, 435 also enable a user to view and select the available plotting variables. If the Relative Size option 425 is selected, a third Variable drop-down list 440 is provided which is identical to the X- and Y-axis drop-down list 430, 435. The user can also choose to fix the axis (or not). The value of fixing the axis is that graphs containing multiple sets of data can be cross-compared without altering the aspect ratio. When this option is turned off, the graph will automatically adjust the aspect ratio and zoom factor to optimize the visibility of the selected data.

Figure 10:
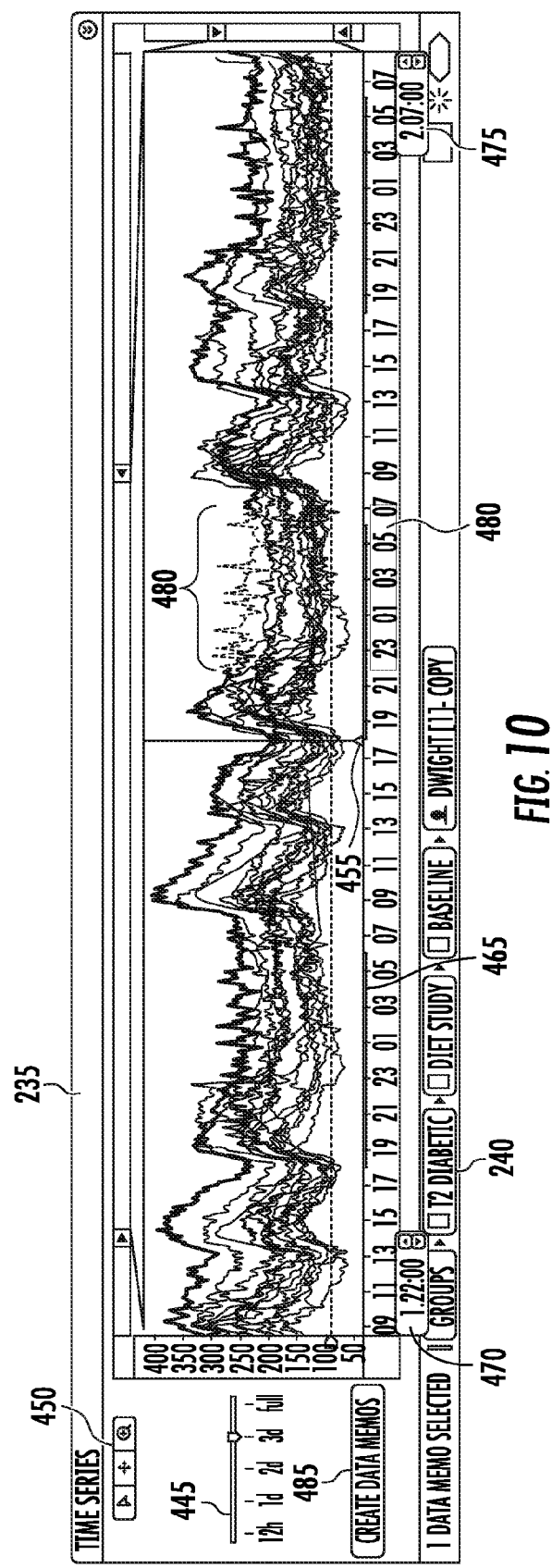
FIG. 10 depicts a Time Series Panel according to the present disclosure.
Figure 11:
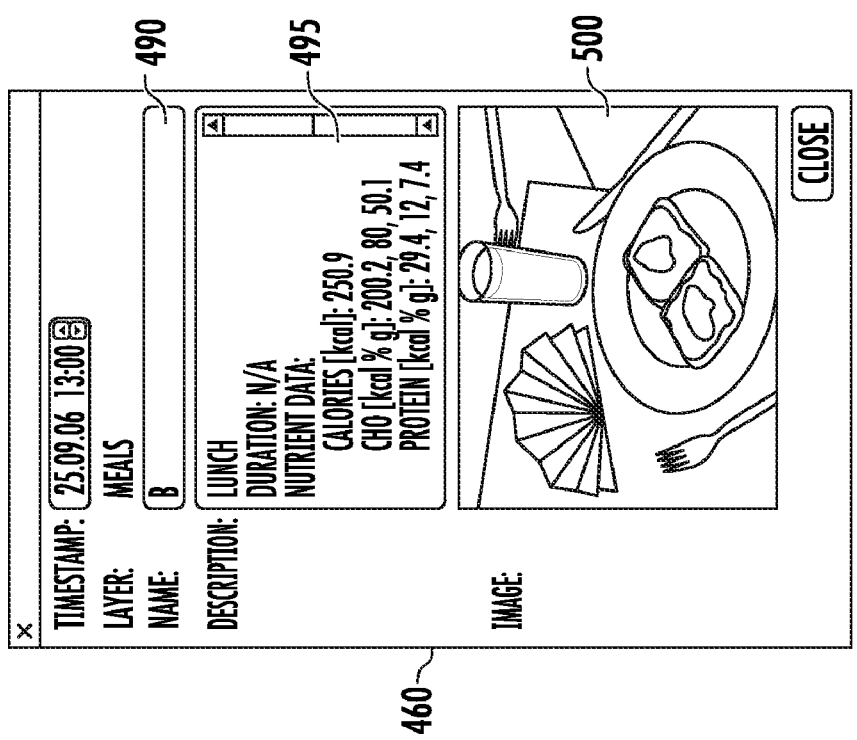
FIG. 11 depicts an Event Panel according to the present disclosure.

FIG. 10 shows in greater details the Time Series Panel 235. From any Workspace 245, 250, 255, a user can open (or close) the Time Series Panel 235 by clicking on its title bar. For example, a user clicking on the title bar for the Time Series Panel 235 in FIG. 7B, will cause the processor to display the panel as shown in FIG. 5. Clicking the title bar again will likewise close the Time Series Panel 235. In addition, the option to maximize or minimize the Time Series Panel 235 is also available for the Source, Groups and Tags panels via small up and down arrows associated with these panels in the left side of the interface. An Incremental zoom slider 445 is used to zoom to a selected time window for the Time Series panel 235 as well as Navigation mode buttons 450 to navigate the viewing area with a combination of Select, Zoom, and Pan tools. A user-created or specified event marker 455 denotes a event type. The user clicks the event marker 455 to open the associated detailed information which is provided in an Event Panel 460 which is illustrated by FIG. 11.

A Day/night indicator 465 is provided such that the evening and overnight period is visibly demarcated on the timeline. It is to be appreciated that all data objects listed in the viewing area 220 will have an associated traces plotted in the Time Series Panel 235 if one exists. In addition, as illustrated by FIG. 7B by the dashed box surrounding one of the data objects which indicates a user selection to the processor, the associated trace is then highlighted (e.g., darkened comparatively to the other data objects' traces) in the Time Series Panel 235 by the processor as shown by FIG. 10. The status bar 240 will also indicated this data object selection. Beginning and end time indicators 470, 475 are also provided. To create a data segment 480, a user clicks and drags in the timeline this highlights the segment from the trace of the data object. The data segment 480 can be saved by clicking on the create Data Memo control 485, wherein the user selected data segment 480 now becomes a Data Memo 170. Other features of the computer program 150 of the present disclosure are also provided which are discussed hereafter.

Custom Event Example

As mentioned, a custom event 455 is a user-specified event marker for an event occurrence that does not exist in the original data structure of the source file (e.g., the .msbx file). As shown by FIG. 11, the user can specify a Tag name for the custom event 455 via a name field 490 as well as enter a short description in a description field 495 and an associate image in an image field 500. In the name field 490, the user may create a new custom Tag name or choose from any previously defined set of tags to facilitate the comparison of similar events across multiple data traces. A practical example of a custom event 455 would be the patient's "wake-up" time, which may be described in hand-written journal format but not embedded in the clinical data itself. Using the custom event feature, a user could take the initiative to add such events to the timeline as shown in FIG. 10, enriching the available context-specific information for use in further analysis.

Any custom event may be used for data memo Alignment, and can be shown or hidden on the timeline in the same way as recorded events for clinical data. As shown in FIG. 7B, all event marker Tags are listed in the Tag section 222 along with an associated number to the right which indicates the number of data objects selected in the Group section 218 having those Tags. For example, as shown of the selected 41 data objects presented in the Baseline, Change, and Steady State groups highlighted in Group section 218, nineteen (19) have an Obese (BMI>30) Tag, and 37 have a Max glucose>130 Tag. Such Tags are also listed in the Tag column 505 provided in the viewing area, whereby a user double clicking on any listed Tag will bring up the Event Panel 460 for the associated Tag. The user can also select a series of Data Memos by choosing a Custom Event and requesting the computer program to "find all instances of this event." The computer program will search the population and produce all Data Memos that carry at least one instance of this event, comparable with a tag search.

Notes

Figure 12:
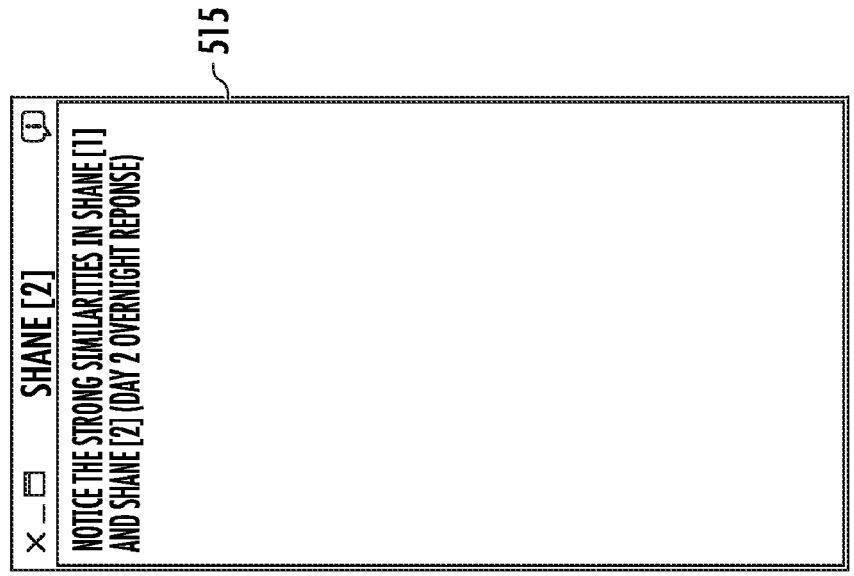
FIG. 12 depicts a Note panel according to the present disclosure.

A user can also associate a contextual note to any data object, such as for example, to any patient data object, to any of the Groups, Tags, Custom Events and other user added metadata that may require explanation. For example, in FIG. 7B, a user only needs to click an info icon 510 next to an object's name to record observations and add notes to a Data Memo or Segment. An object that has an associated note will display a darkened info icon. The user can view and add notes to Groups from the Select workspace 245 when working in Hierarchical view. A user can access notes in the Visualize workspace 250, by right-clicking on any object to open a control selection menu which listed among other things an option to create a note. The user selects the create note option, which then causes the processor to present to the user as a pop-up on the display a note box. The note box 515 is shown by FIG. 12 in which the user may enter information. Notes can be assigned to individual Data Memos, Groups, Tags or Custom Events. The purpose of notes is to aid in the interpretation of a session file, i.e., to explain the logic by which the investigator assigned certain metadata or defined a certain Tag's properties. For example, the investigator makes a Tag called "hyperglycemia" and in an associated note they explain: hyperglycemia is defined as "glucose above 180 mg/dL." These definitions are, of course, made at the user's discretion and are not absolutely factual. The computer program makes no judgment about how the user defines and/or assigns meaning. Evaluation must occur through peer review, as with any research endeavor.

Creating Custom Groups

To protect the integrity of the source data, the present disclosure incorporates extensive custom grouping and segmenting options that allows the user to focus on any combination or cross-section of recorded study data. The user creates groups using one of the following methods. The specific value of Custom Groups is to provide the user with a filing system by which they can organize data according to a logic that best suits their mental model and their research question.

The first method is by object selection. With reference to FIG. 7A, the user can choose one or more of data objects 350 from the viewing area 220. The user Shift+click in the viewing area 220 to select a contiguous range of objects, and then Ctrl+click to add or remove objects from the current selection. From the Select workspace 245, the user drags and drops the selected objects from the viewing area 220 onto an empty area of the Group section 218, right clicks and selects an [Copy Selected To→New Group] button in a pop-up control selection panel, uses the menu command [Group>Create New Group Using Selected], or keyboard shortcut Ctrl+G. At any time, the user can also drag and drop selected objects from a table into an existing Group to add to that Group. From the Visualize or Analyze workspaces, the user can use the menu command [Group>Create New Group Using Selected] (Keyboard shortcut Ctrl+G). The new Group will then be presented in the Group section 218 as named by the user.

The number that appears next to the Group (i.e.) folder reflects the number of Data Memos (i.e. data objects) present at that level only: the number is not a cumulative count of Data Memos contained in any subgroups of the current Group. It is to be appreciated any Group folder within the Source Column can be dragged and dropped to change its order or position in the displayed list of Group section 218, such as to make hierarchies with nested Groups (i.e., a Group within a Group). It is to be appreciated that any user changes to the structure of the hierarchy via user-edits, are immediately reflected in what is displayed on the display; and the current structure of the hierarchy is stored in memory. Likewise, any Data Memo or data object listed in the viewing area 220 can be dragged and dropped or copied into any Group. It is to be appreciated also that multiple (successive) copies of Data Memos behave as unique entities within the Group hierarchy, whereby a unique Data Memo can only reside in one Group. However, a user can make additional copies to place a Data Memo in more than one Group. A user can also color code each Group or let the processor automatically color code the Groups to help differentiate Data Memos.

It is to be appreciated that Groups enable the user to organize data according to their personal mental model and research objectives. There are many different, valid ways to organize identical data, each offering distinct advantages that are more or less suited to specific research questions. Often, there is no single "best" way to organize data because research questions have different requirements for organization and analysis. Consider a series of Data Memos containing time-series glucose data that is associated with specific meal events. One user may organize this data according to the time of day and nutrient composition of the meals. Another user may organize the same Data Memos according to the overall magnitude (AUC) of the associated glycemic response. Yet another user may categorize the same data according to the length of time required for the subject's glucose to return to baseline. The preferred method depends upon the research question that the user wishes to explore with the data.

By naming and assigning color to Groups (which is inherited by members of that Group), the user can much more easily identify the Group affiliation of Data Memos in the workspaces. This feature is extremely valuable when multiple Groups are used to indicate multiple types of data. For example, in the Analyze workspace, the use of color to demarcate Groups makes the members of a bubble graph easier to interpret because the members of different Groups are visually distinguishable. The use of color to identify Group assignment is especially effective in combination with the Query bar, where Groups in the current selection are indicated along with their color assignments (like a "legend").

Through the creation and organization of Groups, the user can build a hierarchy of data that contains valuable information about how the data is structured. For example, Groups which are subsets of other Groups can be thought of as subcategories. For example, "dinner" could be a subcategory of the group "meal." Placed in the hierarchy below the Group "T2 diabetics," we can infer that members of the Group "dinner" are Data Memos representing dinner meals consumed by T2 Diabetics. Group hierarchies create a form of tree diagram with roots (primary Group), branches (subGroups) and leaves (members). The only key distinction is that no inheritance is imposed on a Group hierarchy by the software; the user is responsible to insure that their method to Group Data Memos is logically and accurate.

The second method is by segment creation. As mentioned above, segment creation refers to the process by which a new Data Memo (a new data object) is created by defining a start point and an end point for a time period that contains associated patient data objects. In another embodiment, it is also possible to create a new Data Memo simply by copying a source file into a Group. From the Time Series Panel 235, with one or more objects selected, the user clicks and drags in the timeline of the Time Series Panel to set data segment markers to the desired range. The chosen time range and the glucose traces to which it applies are highlighted in orange. The user then clicks the Data Memo control (i.e., button) 485, as already explain in reference to FIG. 10. It is to be appreciated that if no data object is selected, a Data Memo will be created for all objects in the active group display in the Time Series Panel 235. The user can also use a Generate Segments function, which allows automated data segment creation around recorded events. With one or more objects selected, the user goes to the menu command [Group>Generate Segments . . . ]. In the dialogue, the user chooses the desired events and time range. If no Data Memo object is selected, the computer program 150 will present an error message that nothing is selected. The user has to select one or more Data Memos before new Data Memos will be created according to the specified segment. Of course, it is possible to "select all" and make Data Memos from all members of the selection (=all members of the Group(s) displayed in the Time Series panel). The computer program 150 also permits the user to rename, delete, and export and import groups and Data Memos.

Creating Tags

As mentioned previously above, the Tag feature of the computer program 150 enables grouping and indexing of user-specified data objects (i.e. Data Memos) based on user-created keywords (i.e. the user defined tags). Tagging provides a flexible, human language-based method to render an increasingly complex body of information easier to search and navigate over time. Users can create and manage keywords (tags) to annotate and classify objects, whereby freely chosen keywords are used instead of a controlled vocabulary. For example, a user can right click next to a Data memo listed in the viewing area 220 in the Tag column 505 (FIG. 7B) to open a pop-up control selection menu. In the same manner of creating a group, the user selects a Assign Tag to Selected→New Tag command, which then cause the processor to create tag from the selected Data Memo. The new Tag then will then be listed in the Tag column 505 after naming by the Tag. Similarly, any Data Memo may receive an existing Tag name from all existing Tags which will be shown by the processor listed below the New Tag option in the control selection menu. In addition, Tags can be renamed by double-clicking a Tags title, in which renaming the Tag causes the new name to be updated for all patient data objects to which the Tag was previously assigned. Multiple Tags can be assigned to any unique Data Memo. In addition, one or more Tags can also be combined to create a diagnostic macro that has a specific plurality of associated Tags. A series of Tags combined into a single macro is equivalent to a diagnostic algorithm, especially when used in combination with Boolean logic. For example, such tagging can be use with a database of patient information and associated diagnostic data to empirically develop and/or test a series of tags that constitute the diagnostic macro.

While providing a potentially powerful classification method with low entry cost, user-specific tag vocabularies are by definition limited by their reliance on the individual user for consistency and structure. As no user is sufficiently organized to Tag everything properly on the first attempt, through iterative tagging, exploring, analyzing, visualizing, sorting, grouping and re-exploring, the appropriate Tag and Group categories become clear as this complex exploratory process is facilitated and supported by the computer program 150. The collaborative evolution of common terminology and concepts among multiple users over time enhances the method's efficacy. Tag data may be visualized in different ways to find and sort information. A set of related Tags (referencing the objects to which they refer) are grouped according to different criteria. The application of Tags and tag sets to objects of interest can greatly increase the user's capacity to recognize and discover related information types emerging over the course of investigation.

Layers

Figure 13:
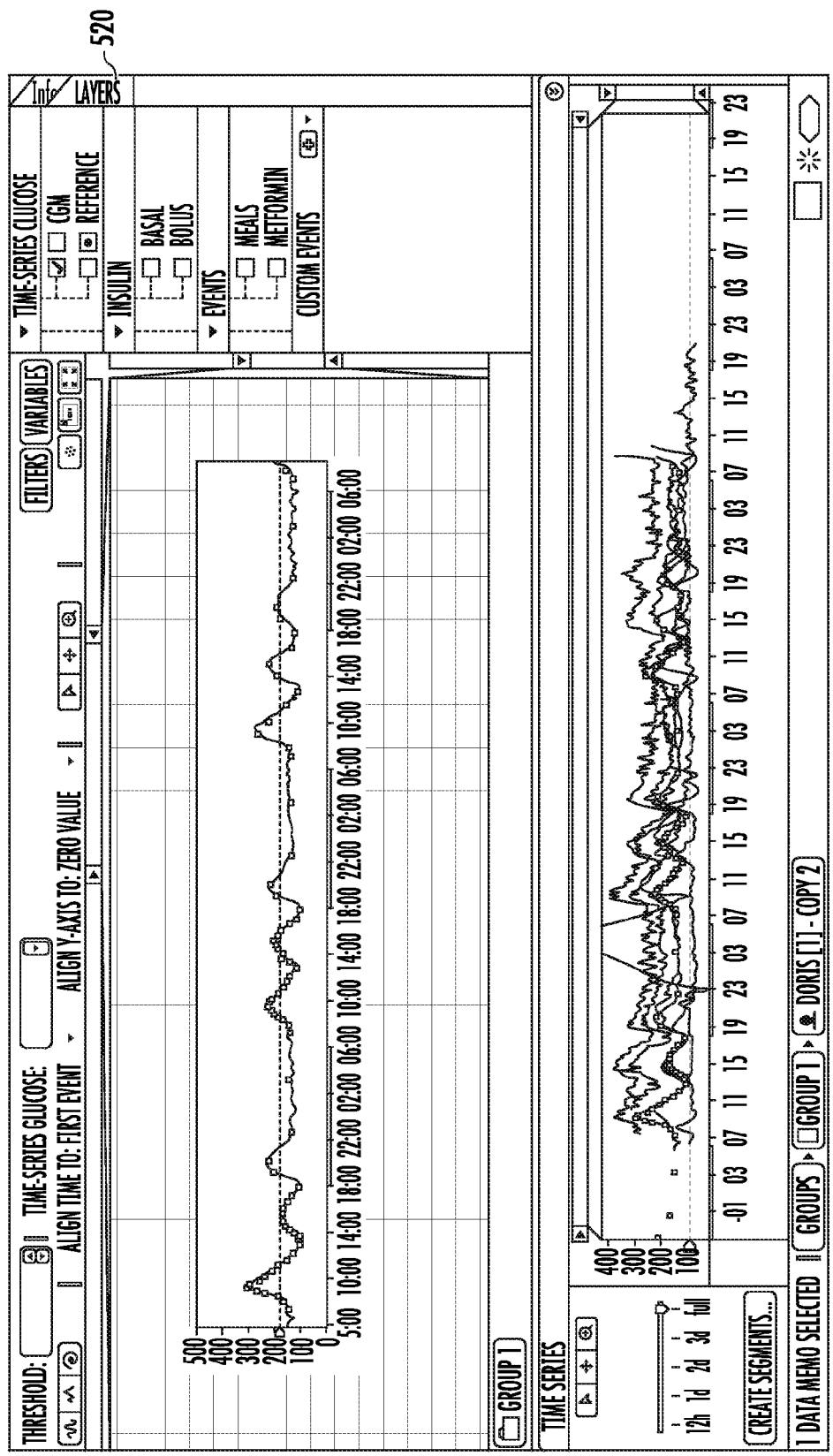
FIG. 13 depicts a layers panel according to an embodiment of the present disclosure.

With reference back to FIG. 5, clicking on a Layers tab 520 will bring to front layers panel depicted by FIG. 13 according to an embodiment of the present disclosure. The principle workspace in which Layers are used is the Visualize workspace, because Layers control the visibility of data. There are instances, however, in which the user would also rely on Layers to control visibility of data in the Time Series panel. Layers are not really relevant to Analyze and Select, wherein data is not plotted in a "visual" format. Therefore, Layers are a user interface feature designed for optimal control over data viewing, wherein multiple data types are present in a single data memo. Layers do not corrupt the source data, but lie on top of them. The best physical metaphor for layers is transparency sheets which can be stacked or removed to view multiple information types in combination. Layers are navigated using the Layers Panel, which provides a series of tools for viewing, annotating and editing layers. The use of layers is useful to visualizing complex data memos in different modes, according to different kinds of study data and research goals. The Layers Panel is a useful navigation tool, not only for managing layers of data, but also to add user observations that enhance the interpretation of the data.

Layers provided by the computer program 150 are a mechanism by which users will invent new forms of data visualization, new interactive techniques of data analysis, and new methods to educate patients on the meaning of their data. Successful layers define, in essence, new visualization and/or analysis methods. Successful layering techniques may lead to the development of commercial products or methods for diagnostic data handling because Layers allow the user to test which types of data are useful to see in combination; and these combinations can be used to develop new methods of patient education and/or physician decision-making and/or reporting patient health to an insurer.

User-specified information may include: New data types, Custom event markers and accompanying descriptions, Images to augment a panel of type "event" or "info", Glucose and/or time masks and accompanying labels, and Color settings to customize a chart or graph for enhanced viewing. Because automatic data loading and handling enforces a degree of generalization onto diverse data, layers recuperate the core value of the present disclosure as a prototyping environment for individual viewing preferences, inventing visualization techniques and generating new ways of seeing data.

Query Groups and Tags

Figure 14:
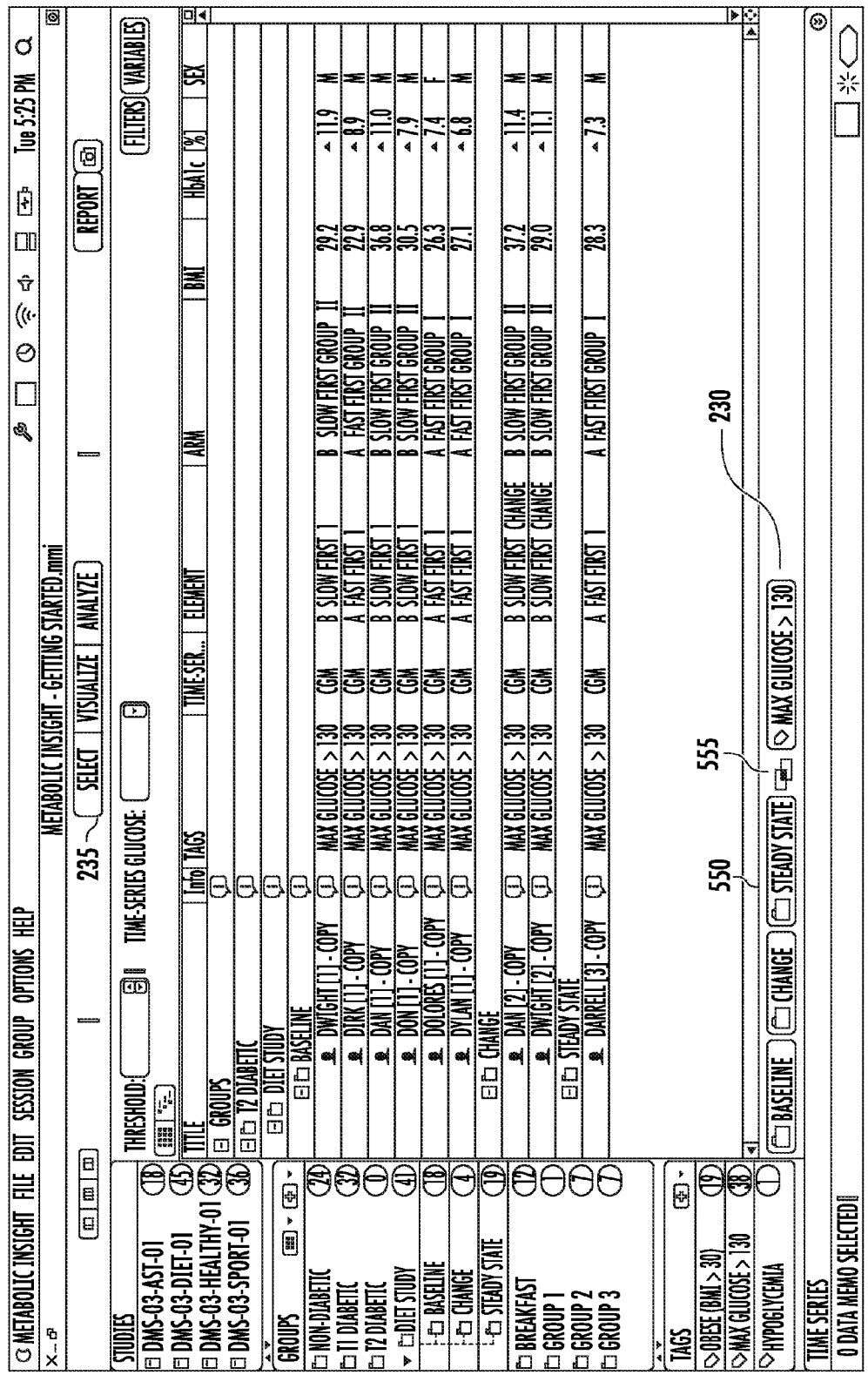
FIG. 14 depicts a query function of Groups and Tags provided by the graphical user interface according to an embodiment of the present disclosure.

With reference to FIG. 14, the user can query Groups and Tags, and combinations thereof. To do so, the user selects one or more Groups containing tagged Data Memos. From the Select workspace 245, the user selects a Group from the Group section 218 that contains tagged Data Memos. For reference, make sure that the Tags column is visible and expanded. Next the user selects a Tag. To maintain the Group selection and additionally select a Tag from the Source Column, the user can ctrl-click (cmd-click) on the user interface. Both the Tag and the previously selected Group are now highlighted as depicted in FIG. 14. The user then can select either an Intersect operation 550 or Union operation 555 on the Query Bar 230. The user clicks the symbol to switch between query operations 550, 555. The Query Bar 230 now displays both the selected Group and Tag, connected by the selected query operation symbol. It is to be appreciated that the Intersect operation 550 is equivalent to the logical operator AND. In other words, the query result will equal only Data Memos that belong to Group1 AND carry Tag1. The Union operation 555 is equivalent to the logical operator OR. In other words, the query result will equal all Data Memos that belong to Group1 OR carry Tag1. The user can add or remove Groups or Tags to the current query using ctrl-click (cmd-click). The order of selection does not affect the results. In addition, multiple Group and Tag queries result in the operation: (Group1 OR Group2 OR Group3 . . . ) AND/OR (Tag1 OR Tag2 OR Tag3 . . . ). In still other embodiments, a user can search one or more Groups using a compound Boolean query made of both logical union and logical intersection operations. For example, a compound Boolean logic can be provided which allows selecting data using a combination of Tags and a combination of logical operators. For example, a search algorithm can be created as follows: (Group: T2 Diabetics) AND ((Tag: obese) OR (Tag: overweight)). The result of this query would yield all members of the Group "T2 Diabetics" who were tagged as EITHER "obese" or "overweight."

Alignment

The Visualize workspace by default is a "desktop" space in which objects can be freely (manually) selected, moved or overlaid. Software-aided alignment features aid specific comparisons and ease the task of manual positioning. Alignment is also an essential step in preparing multiple data memos for averaging e.g. Averaged Curves. Data memos in Time Series mode can be aligned in the following ways: Glucose alignment can simply be turned on or off; Time alignment may include options such as: 24 h modal day (clock time), modal week (clock time+weekday), modal month (clock time+weekday+date distribution); and Event alignment may include options such as the choice of specific event type and occurrence. Any recorded event or custom event may be used for alignment. A Trace feature alignment may include options such as automatic alignment to a statistically defined point in the glucose trace such as maximum or minimum glucose.

Target Range Analysis

Target range analysis feature supports the definition and medical interpretation of meaningful glycemic ranges and event duration with the goal of interpreting the significance of CGM curves for a specific patient or patient population. This feature is especially suited to in-depth analysis of postprandial patterns and the exploration of metabolic dynamics around defined event types, and builds upon the functionality of the layers. The following features are to be noted. The glucose axis can be partitioned into a series of contiguous ranges by defining one or more thresholds, producing a Glucose Mask. The time axis can similarly be partitioned into contiguous periods using point markers, producing a Time Mask. The combination of a glucose mask and time mask creates a matrix of Regions. The glucose trace that passes through a particular region can be characterized with calculated values. Glucose and time mask settings can be saved and applied to multiple data memos. This feature provide the following labeling and customization: (A) Names ("Tags") and color can be assigned to any user-defined range or threshold (for glucose masks); period or point (for time masks); (B) Tags can also be assigned to regions created by a combined glucose and time mask; (C) Tags can be shown or hidden according to viewing options; for example overlaying the data as a label; and (D) Values in a range, period or region can be highlighted. The user may create a new custom tag or choose from any previously defined set of tags to facilitate the comparison of similar observation regions across multiple data traces. Example tag sets are as follows. Glucose thresholds: Hypoglycemia, Fasting, Normoglycemia, and Hyperglycemia. Time points: Maximum peak, Secondary peak, Minimum valley, and Return to fasting. Regions: Fast meal postprandial target, Optimum bolus point, and Target bedtime zone.

Shape Memo

Figure 15:
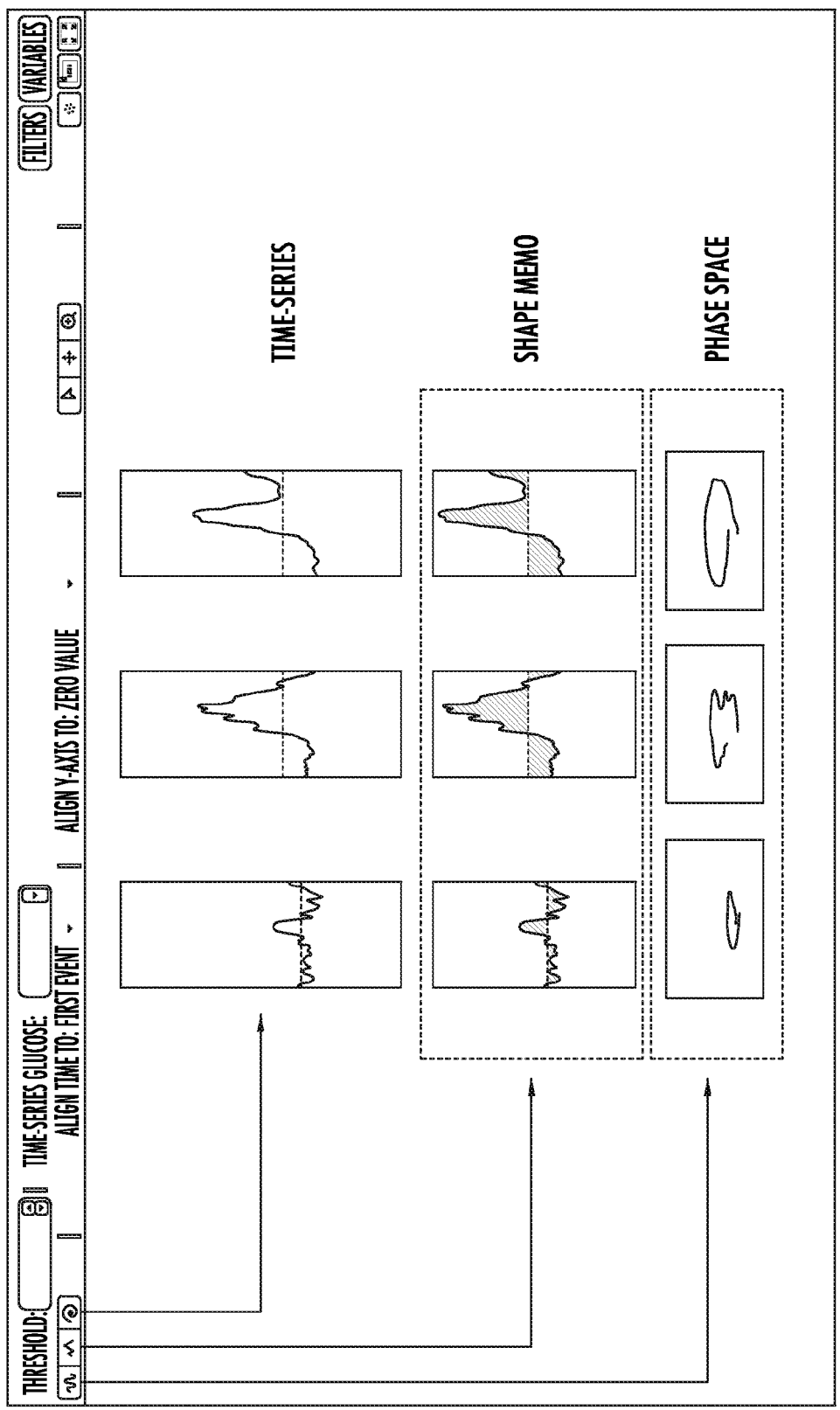
FIG. 15 depicts a sample Shape Memo which promotes the observation of context-specific glucose dynamics according to the present disclosure.

Raw CGM curves and standard timelines are not immediately suitable to differentiating meaningful time/data intervals linked to patient behavior. As shown by FIG. 15, a Shape Memo is designed to promote the observation of context-specific glucose dynamics. It is to be appreciated that "Shape Memo" is a user-friendly application based on the comparison of "Data Memos." A "shape memo" object is, in effect, the same thing as a "data memo" with an especially designed appearance and behavior to aid the user's engagement and interpretation of the data memo. In one embodiment, a Shape-Memo method relies on visual recognition, comparison, and differentiation of CM metadata through Shapes. Employing a graphic shape vocabulary gives non-professional users a way to intuitively evaluate patterns in complex CGM data. It is to be appreciated that the Shape Memo benefits from feature improvements of Target Range Analysis, Alignment, Averaged Curves, and Enhanced File Management. Some points to note: Shapes read as "mountains" and "valleys" in function of the defined baseline. Relative comparisons are preferred to absolute values. Aspect ratio (time and glucose resolution) remains consistent for displaying all Shapes. Relative distortion between displays undermines meaningful analysis and comparison. Start and stop points can be defined either as time or bG value. Standard recording periods (1 hour segments) are preferred for consistent display and comparison. Multiple recordings of similar events are encouraged. It is to be appreciated that Shape Memo is basically iAUC representation where the Threshold is user defined; and the resulting shapes are named, tagged and organized by the user as a "shape grammar" of meaningful time-series data episodes. It is to be appreciated that one of advantages of the Shape Memo is the user-assignment of meaning to these segments, i.e. "this 4 hour shape means lunch," wherein the meaningful Shape Memo object is then saved in device memory. Stored Shape Memos can be updated and evolved by averaging saved data with new events of the same meaning, such as subsequent events that are designated as "lunch" by the user. Shape Memo objects can be organized in memory using hierarchical files; and tagged by the user to describe notable aspects of their significance, such as "large" large, "pizza" lunch, "skipped" lunch, etc. Shape Memo data objects can also be recalled from memory and used as visual-analytical templates on the background of an active timeline of a CGM device, whereby currently recording glucose is compared against previously recorded glucose (the Shape Memo) and differences between the two "shapes" are supported by device intelligence.

Statistical Aids

Selected values can be calculated for an entire data memo according to the applied glucose and time mask settings (i.e. for all regions). Probed regions and associated values can be identified by highlights in multiple views and relevant formats in the computer program 150. Calculated values can be viewed in different ways according to user preferences. Viewing options may include: direct overlay on the data trace, in a table format, or represented with appropriate information graphics when applicable. Statistics generated by Target Range Analysis can be "carried over" and plotted in the Analyze workspace, as well as exported via Reporter to charts. Example values/statistics are as follows: AUC, iAUC, Average Slope, Standard deviation, Min/Max glucose, Mean glucose, % measurements in range/period, % measurements above, below or outside range/period, Absolute time spent in range/period, Absolute time spent above, below or outside range/period, and Glycemic Variability: MAGE, ADRR, LBGI, HBGI, and SD.

Expanded Views and Non-Glucose Time Series

As an alternate method to visualize Layer data, the computer program 150 also permits Expanded Views and Non-Glucose Time Series views. For example, a time mask, which can be used for modal day analysis to measure and compare the duration of significant patterns (such as time to peak) with other event occurrences or types, can be provided. Example event tags are as follows: Medication, Insulin bolus, Hypoglycemia, Menstruation, Meal, Water, Non-water beverage, Alcoholic beverage, Physical activity, Sports, Illness/Stress, and Sleep. Multiple glucose traces may be overlaid or expanded for side-by-side comparison. Expanded views, in which a time mask can also be used to focus the observation window of other recorded time series occurring during the same period (e.g., insulin dosages or specific physiological parameters associated with event types, e.g. heart rate in association with sports) can also be provided. When applying a saved time mask to new data, the user can align defined points of interest with events or specific features of a given trace. The offset (relative to the originally defined 24 h scale) is indicated. However, it is to be appreciated that the Expanded Views, including non-glucose time series, are basically the same thing as Layers, i.e., different data types. The only difference is that here, the Layers are not overlaid but shown adjacent—i.e., in "expanded view."

Average Curves

As patterns are identified within or across individuals, groups or populations, it becomes desirable to enable multiple data segments to be collectively handled and analyzed with ease. The Averaged Curves function achieves these goals by creating a separate "composite" object from multiple Data Memos, and is helped by the functionality of Alignment. An Averaged memo benefits from the same functionality available to single data memos, but has the following unique properties: Combines multiple subjects in an averaged view, Combines multiple time periods that do not share the same clock-time, and Stores additional statistical information about the averaged data. To distinguish an Averaged Curve from ordinary data memos it is designated with a special data memo type that is stored with its identifying information.

The following features are noted. The active metabolic dynamics indicator of two or more Data Memos can be averaged to form a new data object. The time axis of Data Memos selected for averaging can be aligned according to any of the methods for Alignment in Visualize. The Data Memos selected for averaging are clipped to the same time duration according to user preferences. As a merged memo constitutes derived data distinct from original source data, it is not represented on the Time Series Panel. All source Data Memos referenced by the merged memo can be easily accessed, and additionally documented through Reporter.

Some of the following viewing options are provided by the computer program 150: (Default) Mathematical average of the curves as a single and interpolated curve (smoothing options to be defined); (A) Averaged curve with standard deviation bars; and (B) "River diagrams" which are averaged curve with a shaded region indicating SD. An additional shaded region defined by outliers.

Polar Coordinates

It is to be appreciated that the computer program 150 enables a user to easily and quickly (via the representation toggles) to explore alternate methods for visualizing time-series glucose data. Key aspects of diabetic health to emphasize include: relative time spent in hyper- versus hypoglycemia; the intensity of hyper- and hypoglycemic events; and tendencies for a patient to have glucose excursions during certain times of day, or certain days of the week. The Polar Coordinate system provides several promising improvements over classic line graph representations of glucose over time, and may aid in improving a physician's ability to evaluate a patient's metabolic dynamics. The polar coordinate graphing system maps data to a circular axis with subdivisions representing hours, days, or weeks. The numeric value of glucose concentration maps to the distance from the center of the circle. Graphical boundaries and/or color may be used to emphasize important thresholds and conditions, such as hyper- or hypoglycemia. This representation provides an inherently intuitive method of evaluating patterns over time due to its parallels with an analog clock. A tutorial example illustrating procedures for practicing the disclosure is now provided hereafter.

V. Use Example

The following tutorial example should not be construed as limiting. This tutorial example assumes that the computer program of the present invention has been installed on a computer or network server, via an installation package which has been either provided on a computer readable medium, or downloaded from a server.

Launch the Application

The user launches the computer program 150 by double-clicking the program icon in a program folder. The first time the user uses the computer program 150, the user will be prompted to enter user name and license key. In one embodiment, the user enters the information provided by email. The application is now unlocked for personal use (the user will not be asked to enter this information for future sessions).

Load Data

At the prompt, the user chooses an available dataset. A status bar indicates progress during the loading process. When all files are read, an animated loading sequence indicates that the program is assembling the data and drawing the interface. In this example, the dataset is DMS-03-DIET-01, DMS-03-HEALTHY-01, and DMS-03-Sport-01. The user may also open a dataset provided in the database using the menu command [File>Open Clinical Data . . . ].

Explore the Viewing Area in Select

When the data is loaded, the user will be in the Select workspace 245 (FIG. 7A), with patient data displayed as a table in the viewing area. By default, the source list shows all of the study subjects available for viewing and analysis in the DMS-03-DIET-01, DMS-03-HEALTHY-01, and DMS-03-Sport-01 datasets. Note the computer program 150 loads all recorded patient datasets for a given study, including patients with partial or incomplete data. The user then uses the table's vertical and horizontal scroll bars to view all subjects and currently active variables. Currently active variables are also shown as numeric ranges in the Filter panel 280, with histograms showing patient population distribution. The Filter panel 280 displays values corresponding to the entire clinical study dataset.

Open the Time Series Panel

The user clicks anywhere on the title bar labeled "Time Series" at the bottom of the application window to Open the Time Series Panel 235. As shown by FIG. 10, the Time Series Panel 235 displays the overlaid continuous glucose traces of all active patients. In addition, by using the Layers panel (FIG. 13), a user can view any time-stamped data associated with the patient data object, such as for example, insulin (measured and/or infused), medication dosing, events, heart rate, etc. The user then clicks on a subject in the table in the viewing area 220 as indicated by FIG. 7B. The corresponding glucose trace is then highlighted in the Time Series Panel 235. It is to be appreciated that passing the cursor of the GUI 200 over a subject in the table without clicking will result in the processor highlighting the corresponding glucose trace, such as in dark grey, in the Time Series Panel 235.

Select a Subset of Subjects

The user then uses a combination of sorting and filtering actions to focus on the subjects and information that is of interest. For example, the user may select all subjects between the ages of 25 and 30 ("Age") with at least 3 days of recorded continuous glucose data ("Duration"—expressed as days: min:sec). To do so, the user clicks the corresponding column header in the table to change the displayed order (ascending or descending). Using the filter panel 280 (FIG. 7A) data objects can be filter out according to the desired numerical threshold (i.e., age 25 to 30) by using the sliders to adjust the upper and lower limits of the desired value range. Alternately, the user can step through value increments using the up/down arrows in the fields or type a value directly into the value fields. Filtered subjects appear grayed in the table and Time Series Panel 235, as depicted by FIG. 7A indicating that they are temporarily excluded from selection or further analysis. The user adjusts the information display settings according to desired preferences using the following actions: (a) change a column's position in the table by dragging the column header; or (b) show or hide columns (variables) by clicking on the Variable button 232 (FIG. 5) at the upper right corner of the table, and check or uncheck variables.

Create a New Group

Upon completing the previous task, the user has a desired number of active subjects in the table. Next to create a new Group, the user does the following steps. First, the user selects all active subjects by using the keyboard shortcut Ctrl+A or manually select multiple subjects from the table using Shift+ click. Active selections appear in blue. Next, the user drags the selected subjects into the Group section 218. A new group folder is created named "Diet Study" which is highlighted. The user can further filter the Group using the Time Series Panel 235. For example, the user may filter out subjects with visibly unreliable data by clicking on the suspect trace to select it and using the corresponding checkbox in the filter column 525 next to the corresponding subject name now highlighted in the table to hide that data object from further analysis.

Manually Create a Data Memo

Next, the user can create a "clean" Data Memo such as, for example, from the subject "Dwight [1]" in FIG. 7B by performing the following steps. First, the user select the "Diet Study" group folder and, with the Time Series Panel 235 open, selects the subject "Dwight [1]" from the list provided in the viewing area 220 which the corresponding trace is highlighted in the Time Series Panel 235 as depicted in FIG. 10. Next, in the Time Series Panel 235, the user clicks to a point of interest and dragging the mouse to activate the a data segment 480. The user may also use the incremental zoom slider 445 to set a fixed time window (12 hours, 1 day, 2 days, 3 days or full, for example) before adjusting with the manual zoom. The marked section of the timeline and the corresponding trace is highlighted. The user may then zoom and pan in the display as necessary to visually reference the glucose trace and adjust the start and stop points to the desired positions (by dragging the markers at their extremities). Clicking again in the timeline resets the markers. When the user is satisfied with the selection, the user uses the Create Data Memo control 485 to save the segment 480 as a Data Memo 170. When the operation is complete, the newly created data segment is highlighted in its saved location, for example as "Dwight [2]-copy." It is to be appreciated that for example, the user can also change the title of Dwight [2]-copy to something more descriptive, such as "Dwight [2] breakfast meal," assign a Tag to Dwight, such as "Hyperglycemic," or create a note for Dwight stating that he suffers from frequent hypo events, etc.

Save the Session

To save the session, the user uses the menu command [File>Save Session . . . ] or keyboard shortcut Ctrl+S which creates a .mmi file. Opening a saved session (i.e., an .mmi file) at a future time will load all groups and settings associated with that session. The user can use saved sessions as incremental "backups" for ongoing experiments by saving under a different (ideally sequential) name. By default, sessions saved with the same name will overwrite previous versions of that session.

Export a Group

The user may use the menu command [Group>Export Group . . . ] or right-click on a group folder and choose the Export option to save a group file (.mmg) separately from a session file (.mmi). Also, the user may import a previously saved group into a session by using the menu command [Group>Import Group . . . ].

VI. Faceted Classification and Findability

File Organization Based on a Faceted Classification

It is to be appreciated that a feature of an embodiment of the present disclosure is that it is able to support two very different strategies of data classification simultaneously. The method described herein can be technically described as a "faceted classification system." A faceted classification system is a method of organizing objects in which the user can chose the order in which categories of classification are presented and the meaning that they impose by their ordering. This free-form method of data classification contrasts with top-down systems such as Linnaean Taxonomy and the Dewey Decimal System, wherein any object found at a lower level in the hierarchy inherits the properties of the object(s) above it; and typically, strict rules define how objects should be classified within an existing structure. In our method of system building, the system itself is subject for design, editing and populating by the user. Data objects do not automatically inherit properties according to predefined or systematic rules (unless these rules are defined by the user, such as Group color or Tag assignments). The criteria by which data is organized and assigned meaning can be flexibly defined and tested by the user according to their needs or way of thinking. The computer program does not make any judgment or assertions about the meaning of the classification system nor the data that it contains, although inheritance of properties may be inferred simply by the logic by which the user chooses to build their Group hierarchy. Inference of inherited traits is useful for guiding the research process, but should be pursued with caution unless the user's logic has been made explicit. Notes are one way that the user can explicitly describe their logic for Group structuring and Tagging.

A faceted system of classification provides the organizational benefits of a hierarchy without imposing the constraints of traditional hierarchical system (in which placement has pre-defined meaning). The method of classification according to an embodiment of the present disclosure is therefore appropriate for ordering data in which the user has his or her own ideas about the data's meaning, as is often the case in exploratory research, wherein a universal theory for meaning does not yet exist. In other words, there is no pre-defined meaning as the computer program 150 enables the user to define their own system of meaning according to the data, their research objectives and their mental model. There are, however, certain rules that define how our methodology is used to build user-defined systems of classification. The rules are described in the following sections.

Data Findability

As used herein, the term "data findability" means navigating and retrieving data within a user-defined structure. Data can be located by searching either the structure (Groups) or the descriptions used to label the data (Tags). For example, a user may specifically assign to a data object a specific Tag used only for the purpose of findability or associate multiple Tags to the data object, and then perform searches using Boolean combinations of the multiple Tags. It is to be appreciated that the apparently simple, but non-obvious fact of locating data within a classification structure may yield new insights by revealing patterns or relationships with other data. The user can thereby gain insights based on the structure by which they choose to organize their data and the position of shared observations within this structure. One good example of data findability can be demonstrated with Tag filtering of the computer program 150.

Figure 16:
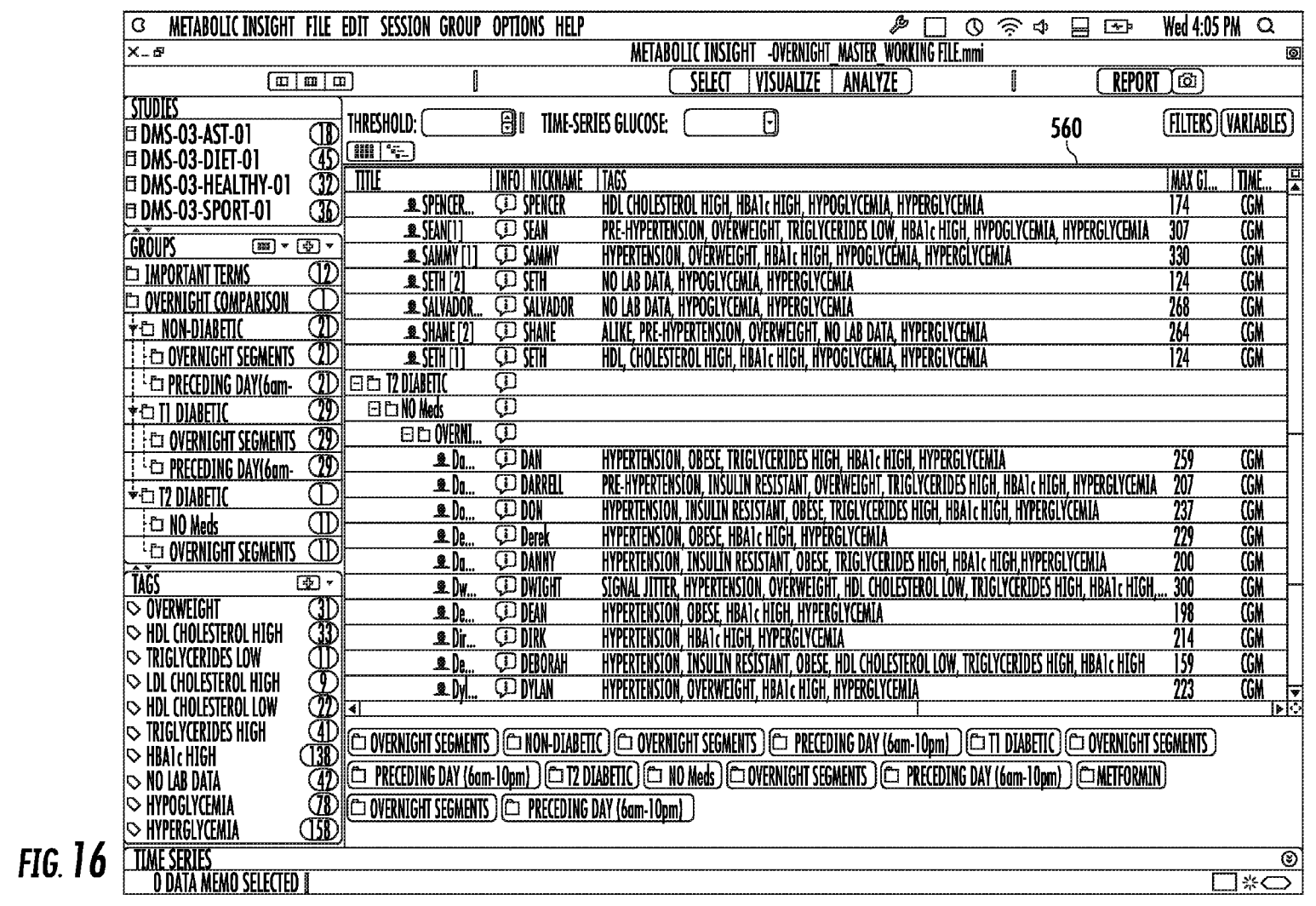

In FIG. 16, the Group "Non-Diabetic" has been has been intersected with the Tag "Pre-Hypertension." Intersecting a Group with a Tag applies a logical AND operation of the Tag onto the Group. Therefore, in the Select Table (center), all members of the Group "Non-Diabetic" who also carry the descriptive Tag "Pre-Hypertension" are showing in the viewing area 220. Scrolling down in the hierarchy will show other members that are not visible in FIG. 16 (large Group and member hierarchies require scrolling to see in their entirety). Also, FIG. 14 depicts intersecting a Group with a Tag to find members with shared properties. Note expanding the Time Series Panel via clicking on the title bar would list all the continuous glucose data associated with these members.

More advanced findability can be achieved using a combination of Tags in a Boolean statement. Boolean statements using a string of Tags can be applied as a complex filter to the members of one or more Groups. For example, we begin with a Group defined as "T2 Diabetics." Based on a high incidence of depression in this patient population, we want to investigate whether certain patients are depressed because (1) Metformin isn't controlling their glucose levels and therefore, they feel helpless; (2) their diet is restricted and therefore, they feel sad; (3) treatment with Metformin is interfering with their depression medication; (4) their depression medication is interfering with the therapeutic effects of Metformin; or (5), their depression is caused by some combination of 1-4. This is a complex query, but The present disclosure can help us to isolate a patient population within a database and these questions systematically. To isolate the members of the population "T2 Diabetics" who are treated with Metformin, following a restricted diet and clinically depressed, we make the following query statement:

T2 DIABETICS AND Metformin AND restricted diet AND clinically depressed,
where that groups are indicated in UPPER CASE; Boolean operators are indicated in UPPER CASE ITALICS and tags are indicated in lower case. This initial Boolean based, query statement will allow a user to find all of the T2 diabetics in the patient population who have the characteristics that the user is looking to understand. Using these filter criteria, the user can define a new Group called "Study Population." Next, the user can try to isolate reasons for their depression. One possible reason is (1) Metformin isn't controlling their glucose levels and therefore, they feel helpless. In order to focus on patients for whom this explanation may apply, the user can further filter people who suffer from uncontrolled diabetes, by the following query statement:

STUDY POPULATION AND (HBA1c>9.0 OR iAUCt>30).

In the above query statement, the user use a combination of Boolean operators, AND and OR because the user wants to filter our population with two tags instead of only one (because the patients do not need to have both characteristics; they only need to have one of the two qualifying characteristics. Both of these Tag criteria are indicators of uncontrolled diabetes; therefore, the results of this filter should be a population of T2 Diabetics who fit all of the criteria that the user is seeking to understand. Continuing with this application of Tag logic to carefully selected Groups, the computer program 150 can help the researcher to identify a highly qualified group of individuals; and to narrow the possible reasons behind their symptoms, in this case, depression.

A second example of findability supported by the computer program 150 can be demonstrated using column sorting in the Select Table. For example, the user can find all Data Memos with a maximum glucose level greater than 180 mg/dL by sorting the column "Max Glucose" 560 from high to low in FIG. 16.

A third example of the computer program 150 supporting data findability is demonstrated by the three distinct workspaces. Select, Visualize and Analyze workspaces 245, 250, 255 support the identification of differences and similarities in diagnostic data by providing alternate views onto the same information. Often, the same data viewed differently will reveal important clues about its significance. The ability to easily view clinical data in numeric, plotted, annotated, statistical and graphical format provides the researcher with numerous options to seek relationships. Initial hypothesis can be recorded in our editable system of data classification (Groups and Tags) for continued exploration and verification through the three workspaces. Such an embodiment of the present disclosure maintains active knowledge of the selected Data Memo(s) across all workspaces, thus making it very easy to navigate without losing the object(s) of interest. Navigating workspaces is especially useful when an outlier is identified.

Having described the disclosure in detail and by reference to specific embodiments thereof, it will be apparent that modifications and variations are possible without departing from the scope of the disclosure defined in the appended claims. For example, although the embodiments have been discussed in terms of using metabolic-related clinical data, the methods described herein could be equally applied to other time-series diagnostic data sets such as galvanic skin response, heart rate, breathing rate, blood oxygen levels, pharmakinetics, gene and/or protein expression, rate of physical activity, tumor growth, viral load, etc., as well as medical data related to events in a patient's life such as eating, sleeping, medication, treatment, etc. In addition, although some aspects of the present disclosure are identified herein as preferred or particularly advantageous, it is contemplated that the present disclosure is not necessarily limited to these preferred aspects of the disclosure.

What is claimed is:

1. An apparatus for viewing and organizing patient data objects of a data structure comprising:
    a display;
    a user interface;
    a memory containing a plurality of patient identifications having associated therewith the patient data objects, said patient data objects including patient physiological data; and
    a processor operably connected to the display, the user interface, and the memory and including a program for causing the processor to display from memory the plurality of patient identifications and associated patient data objects of each patient identification on the display for selection via the user interface, to assign in memory the associated patient data objects of selected patient identifications to a designated group in a group hierarchy of other designated groups, to display from memory the patient data objects assigned to the designated group on the display for selection via the user interface, to assign in memory selected patient data objects to a user-defined tag which characterizes the selected patient data objects to a user-specified event undefined originally in the data structure, wherein the user-defined tag is one or more descriptive keywords which annotate and classify the selected patient data objects to the user-specified event, to receive a specified user-defined tag selected via the user interface from other displayed user-defined tags each characterizing a selection of patient data objects to a different user-specified event undefined originally in the data structure, and to retrieve from memory and display on the display all patient data objects in the group hierarchy that are assigned the specified user-defined tag;

wherein the program further causes the processor to create in memory a data segment from a time series provided in the patient data objects; and wherein the program further causes the processor to permit both a selection via the user interface of one or more of the displayed user-defined tags contained in the chosen one or more designed groups and of a query choice which instructs the processor to display on the display as a group the patient data objects belonging to either a union of the one or more chosen designed groups and a received selection of the one or more displayed user-defined tags, or an intersection between the one or more chosen designed groups and the received selection of the one or more displayed user-defined tags.

2. The apparatus according to claim 1, wherein the program further causes the processor to list the group hierarchy on the display for permitting a choosing of one or more designated groups via the user interface and to display all user-defined tags assigned to the patient data objects assigned to the chosen one or more designed groups on the display.

3. The apparatus according to claim 1, wherein the program further causes the processor to display a number adjacent the specified user-defined tag which reflects a cumulative count of all patient data objects carrying the specified designed tag throughout the group hierarchy.

4. The apparatus according to claim 1, wherein the program further causes the processor to permit contextual notes entered via the user interface to be associated in memory with patient data objects.

5. The apparatus according to claim 1, wherein the program further causes the processor to display a listing of all user-defined tags in the group hierarchy for selection of one or more user-defined tags via the user interface and to display all data objects assigned the selected user-defined tags.

6. The apparatus according to claim 5, wherein deleting a tag removes the tag and all its-associations of the deleted tag to all assigned patient data objects, wherein the deleting does not delete the patient data objects from any assigned designated group.

7. The apparatus according to claim 1, wherein the designated group is a sub-group of one or more of the designated groups.

8. The apparatus according to claim 1, further comprising a data source for providing to the memory selected ones of the plurality of patient identifications and the associated patient data objects when requested by the processor.

9. The apparatus according to claim 1, further comprising a data source storing the plurality of patient identifications and associated patient data objects grouped according to a clinical study, wherein the memory receives selected ones of the plurality of patient identifications and the associated patient data objects from the data source according to which one of the at least one clinical study is requested by the processor to be received from the data source.

10. The apparatus according to claim 1, wherein the program further causes the processor to display the group hierarchy on the display.

11. The apparatus according to claim 1, wherein the program further causes the processor to display on the display one of a plurality of workspaces selected via the user interface, said workspaces include a data selection workspace which presents the patient data objects in a table, a visualize workspace which presents glucose traces derived from the patient physiological data provided in the patient data objects, and an analyze workspace which presents a graph of the patient data objects plotted according to variables which further characterize the patient data objects.

12. The apparatus according to claim 11, wherein the patient data objects used by the processor in a selected workspace is selected via the user interface from at least one of the designated group, the designated groups, and the specified user-defined tag.

13. The apparatus according to claim 11, wherein the program further causes the processor to present on the display a variable selection panel for selecting the variables.

14. The apparatus according to claim 11, wherein the program further causes the processor to present on the display a time series panel which displays an overlay of the glucose traces.

15. The apparatus according to claim 11, wherein the program further causes the processor to highlight one or more of the patient data objects presented in a selected workspace on the display when chosen via the user interface and to maintain the highlighting of the one or more patient data objects when presenting another one of the workspaces when selected via the user interface.

16. The apparatus according to claim 11, wherein the patient identifications and the patient data objects are selectable via the user interface and assignable in memory to a new designated group and to a new user-defined tag from any one of the workspaces.

17. A method of organizing patient data objects using a data processing system having a display, a user interface, a memory, and a processor operably connected to the display, the user interface, and the memory, said method comprising:

receiving into the memory a plurality of patient data objects organized via a clinical data structure from a data source; and operating the processor to:

display from memory the plurality of patient identifications and associated patient data objects of each patient identification on the display for selection via the user interface, assign in memory the associated patient data objects of selected patient identifications to a designated group in a group hierarchy of other designated groups, display from memory the patient data objects assigned to the designated group on the display for selection via the user interface, assign in memory selected patient data objects to a user-defined tag which characterizes the selected patient data objects to a user-specified event undefined originally in the clinical data structure, wherein the user-defined tag is one or more descriptive keywords which annotate and classify the selected patient data objects to the user-specified event, receive a specified user-defined tag selected via the user interface from other displayed user-defined tags each characterizing a selection of patient data objects to a different user-specified event undefined originally in the data structure, retrieve from memory and display on the display all patient data objects in the group hierarchy that are assigned the specified user-defined tag, create in memory a data segment from a time series provided in the patient data objects, and permit both a selection via the user interface of one or more of the displayed user-defined tags contained in the chosen one or more designed groups and of a query choice which instructs the processor to display on the display as a group the patient data objects belonging to either a union of the one or more chosen designed groups and a received selection of the one or more displayed user-defined tags, or an intersection between the one or more chosen designed groups and the received selection of the one or more displayed user-defined tags.

18. A non-transitory computer readable media containing a program for displaying and organizing patient data objects on a display device of a computer system, the patient data objects being obtained from a data source associated with the computer system, said program operates a processor of the computer system to receive into memory the plurality of patient data objects organized via a clinical data structure from a data source, display from memory the plurality of patient identifications and associated patient data objects of each patient identification on the display for selection via the user interface, assign in memory the associated patient data objects of selected patient identifications to a designated group in a group hierarchy of other designated groups, display from memory the patient data objects assigned to the designated group on the display for selection via the user interface, assign in memory selected patient data objects to a user-defined tag which characterizes the selected patient data objects to a user-specified event undefined originally in the clinical data structure, wherein the user-defined tag is one or more descriptive keywords which annotate and classify the selected patient data objects to the user-specified event, receive a specified user-defined tag selected via the user interface from other displayed user-defined tags each characterizing a selection of patient data objects to a different user-specified event undefined originally in the data structure, retrieve from memory and display on the display all patient data objects in the group hierarchy that are assigned the specified user-defined tag, create in memory a data segment from a time series provided in the patient data objects, and permit both a selection via the user interface of one or more of the displayed user-defined tags contained in the chosen one or more designed groups and of a query choice which instructs the processor to display on the display as a group the patient data objects belonging to either a union of the one or more chosen designed groups and a received selection of the one or more displayed user-defined tags, or an intersection between the one or more chosen designed groups and the received selection of the one or more displayed user-defined tags.

* * * * *

UNITED STATES PATENT AND TRADEMARK OFFICE
CERTIFICATE OF CORRECTION

PATENT NO. : 8,392,419 B2
APPLICATION NO. : 12/949201
DATED : March 5, 2013
INVENTOR(S) : Kelly Heaton et al.

It is certified that error appears in the above-identified patent and that said Letters Patent is hereby corrected as shown below:

In the Specification

Col. 1, Line 59, "The advantage of such as system" should read --The advantage of such a system--;

Col. 2, Lines 13-14, "the same Tag concept" should read --the same tag concept--;

Col. 3, Lines 8-9, "would easily overwhelmed" should read --would easily overwhelm--;

Col. 5, Line 58, "one of the designated group" should read --one of the designated groups--;

Col. 7, Line 36, "depicts a analyze" should read --depicts an analyze--;

Col. 7, Line 43, "Note panel" should read --Note Panel--;

Col. 7, Line 45, "layers panel" should read --Layers Panel--;

Col. 8, Line 14, "instructions contain in the code" should read --instructions contained in the Code--;

Col. 9, Line 4, "could comprises" should read --could comprise--;

Col. 11, Line 34, "hyperglycaemic" should read --hyperglycemic--;

Col. 12, Line 9, "step 140 classify them via" should read --step 140 classifying them via--;

Col. 12, Lines 24-25, "user can generated" should read --user can generate--;

Col. 12, Lines 41-42, "The use of computer program" should read --The use of a computer program--;

Col. 13, Line 24, "it's defined start point or after its defined end point.." should read
--its defined start point or after its defined end point.--;

Col. 16, Line 10, "but in other embodiment" should read --but in other embodiments--;

Signed and Sealed this
Twenty-fourth Day of September, 2013

Teresa Stanek Rea
*Deputy Director of the United States Patent and Trademark Office*

CERTIFICATE OF CORRECTION (continued)
U.S. Pat. No. 8,392,419 B2

Col. 17, Line 23, "Memo is that is supports" should read --Memo is that it supports--;

Col. 18, Line 38, "clinical trails" should read --clinical trials--;

Col. 18, Line 54, "at user discretion)" should read --at user discretion).--;

Col. 19, Line 2, "Discuss of" should read --Discussion of--;

Col. 21, Lines 46-47, "alternative hid or shown" should read --alternatively hides or shows--;

Col. 22, Line 11, "are each handled as separate data object" should read --are each handled as a separate data object--;

Col. 22, Lines 18-19, "will automatically retrieved" should read --will automatically retrieve--;

Col. 22, Line 33, "are to be display by" should read --are to be displayed by--;

Col. 22, Line 42, "but can seen via" should read --but can be seen via--;

Col. 22, Line 59, "exclude object" should read --exclude objects--;

Col. 24, Line 37, "has be" should read --has been--;

Col. 25, Line 6, "enter a value" should read --entering a value--;

Col. 25, Lines 59-60, "a event type" should read --an event type--;

Col. 26, Line 6, "will also indicated this" should read --will also indicate this--;

Col. 26, Line 9, "timeline this highlights" should read --timeline and this highlights--;

Col. 28, Lines 50-51, "as already explain" should read --as already explained--;

Col. 29, Line 14, "selects a Assign Tag" should read --selects an Assign Tag--;

Col. 29, Line 15, "which then cause" should read --which then causes--;

Col. 29, Line 16, "to create tag" should read --to create a tag--;

Col. 29, Line 17, "then will then be" should read --will then be--;

Col. 29, Line 30, "can be use" should read --can be used--;

Col. 31, Line 38, "This feature provide" should read --This feature provides--;

Col. 33, Line 24, "Combines" should read --combines--;

Col. 33, Line 25, "Stores" should read --stores--;

Col. 33, Line 56, "certain times of day" should read --certain times of the day--;

CERTIFICATE OF CORRECTION (continued)
U.S. Pat. No. 8,392,419 B2

Col. 35, Line 1, "can be filter out" should read --can be filtered out--;

Col. 35, Line 35, "First, the user select the" should read --First, the user selects the--;

Col. 35, Line 41, "activate the a data" should read --activate the data--;

Col. 36, Line 45, "of traditional hierarchical system" should read --of a traditional hierarchical system--;

Col. 37, Line 8, "has been has been" should read --has been--;

Col. 37, Line 34, ", but The present" should read --, but the present--; and

Col. 37, Line 57, "the user use a" should read --the user uses a--.